(12) United States Patent
Gerber et al.

(10) Patent No.: US 10,064,986 B2
(45) Date of Patent: Sep. 4, 2018

(54) RECHARGER FOR RECHARGING ZIRCONIUM PHOSPHATE AND ZIRCONIUM OXIDE MODULES

(71) Applicant: Medtronic, Inc., Minneapolis, MN (US)

(72) Inventors: Martin T. Gerber, Maple Grove, MN (US); Christopher M. Hobot, Tonka Bay, MN (US); David B. Lura, Maple Grove, MN (US); Kanjimpuredathil Muralikrishna Menon, Bangalore (IN); Kaustubh R. Patil, Bangalore (IN); Mahesh Parameswaran, Bangalore (IN); Rohit Kumar Narula, Dehra Dun (IN); Ramkumar Jeyachandran, Bangalore (IN)

(73) Assignee: Medtronic, Inc., Minneapolis, MN (US)

( * ) Notice: Subject to any disclaimer, the term of this patent is extended or adjusted under 35 U.S.C. 154(b) by 204 days.

(21) Appl. No.: 15/143,458

(22) Filed: Apr. 29, 2016

(65) Prior Publication Data
US 2016/0243299 A1 Aug. 25, 2016

Related U.S. Application Data

(63) Continuation-in-part of application No. 14/722,068, filed on May 26, 2015, which is a continuation-in-part
(Continued)

(51) Int. Cl.
*B01D 11/00* (2006.01)
*A61M 1/16* (2006.01)
(Continued)

(52) U.S. Cl.
CPC .......... *A61M 1/1696* (2013.01); *A61M 1/169* (2013.01); *B01J 20/0211* (2013.01);
(Continued)

(58) Field of Classification Search
None
See application file for complete search history.

(56) References Cited

U.S. PATENT DOCUMENTS 3,840,835 A 10/1974 Kussy et al.
3,850,835 A 11/1974 Marantz
(Continued)

FOREIGN PATENT DOCUMENTS

CN 1487853 A 11/2000
EP 2446908 5/2012
(Continued)

OTHER PUBLICATIONS

European Search Report and Supplemental Search Report in European Application No. 14865374.4 dated Jun. 12, 2017.
(Continued)

*Primary Examiner* — Richard C Gurtowski
(74) *Attorney, Agent, or Firm* — Kenneth Collier; Rogers Hahn

(57) ABSTRACT

Systems and methods for recharging zirconium phosphate and zirconium oxide in reusable sorbent modules are provided. The systems and methods provide for recharging any combination of zirconium phosphate and/or zirconium oxide sorbent modules. The systems and methods also provide for linkage of multiple rechargers for sharing of infrastructure.

22 Claims, 11 Drawing Sheets

Related U.S. Application Data of application No. 14/722,119, filed on May 26, 2015, which is a continuation-in-part of application No. 14/642,847, filed on Mar. 10, 2015, which is a continuation-in-part of application No. 14/261,651, filed on Apr. 25, 2014, now Pat. No. 9,895,477.

(60) Provisional application No. 62/077,159, filed on Nov. 7, 2014, provisional application No. 62/016,613, filed on Jun. 24, 2014, provisional application No. 61/941,672, filed on Feb. 19, 2014, provisional application No. 61/909,372, filed on Nov. 26, 2013.

(51) Int. Cl.
| | | |
|---|---|---|
| *B01J 39/12* | (2006.01) | |
| *B01J 41/10* | (2006.01) | |
| *B01J 20/34* | (2006.01) | |
| *B01J 20/02* | (2006.01) | |
| *B01J 39/09* | (2017.01) | |
| *B01J 49/53* | (2017.01) | |
| *B01J 49/57* | (2017.01) | |
| *B01J 49/60* | (2017.01) | |

(52) U.S. Cl.
CPC ....... *B01J 20/3475* (2013.01); *B01J 20/3483* (2013.01); *B01J 39/09* (2017.01); *B01J 39/12* (2013.01); *B01J 41/10* (2013.01); *B01J 49/53* (2017.01); *B01J 49/57* (2017.01); *B01J 49/60* (2017.01); *A61M 2205/3317* (2013.01); *A61M 2205/3324* (2013.01); *A61M 2205/3331* (2013.01); *A61M 2205/3334* (2013.01); *A61M 2205/3368* (2013.01)

(56) References Cited

U.S. PATENT DOCUMENTS

| | | | |
|---|---|---|---|
| 4,192,748 | A | 3/1980 | Hyden |
| 4,687,582 | A | 8/1987 | Dixon |
| 6,579,460 | B1 | 6/2003 | Willis |
| 2002/0112609 | A1 | 8/2002 | Wong |
| 2003/0097086 | A1 | 5/2003 | Gura |
| 2005/0056592 | A1 | 3/2005 | Braunger |
| 2005/0274658 | A1 | 12/2005 | Rosenbaum |
| 2006/0241543 | A1 | 10/2006 | Gura |
| 2008/0011664 | A1 | 1/2008 | Karoor |
| 2008/0241031 | A1 | 10/2008 | Li |
| 2009/0101552 | A1 | 4/2009 | Fulkerson |
| 2009/0282980 | A1 | 11/2009 | Gura |
| 2010/0004588 | A1 | 1/2010 | Yeh |
| 2010/0078387 | A1 | 4/2010 | Wong |
| 2010/0312172 | A1 | 12/2010 | Hoffman |
| 2011/0017665 | A1 | 1/2011 | Updyke |
| 2011/0048949 | A1 | 3/2011 | Ding |
| 2011/0171713 | A1 | 7/2011 | Bluchel |
| 2011/0272352 | A1 | 11/2011 | Braig |
| 2011/0297593 | A1 | 12/2011 | Kelly |
| 2012/0273354 | A1 | 11/2012 | Orhan et al. |
| 2013/0199998 | A1 | 8/2013 | Kelly |
| 2013/0213890 | A1 | 8/2013 | Kelly |
| 2014/0158588 | A1 | 6/2014 | Pudil |
| 2014/0158623 | A1 | 6/2014 | Pudil |
| 2015/0108069 | A1 | 4/2015 | Merchant |
| 2015/0251161 | A1 | 9/2015 | Pudil |
| 2015/0251162 | A1 | 9/2015 | Pudil |
| 2015/0367055 | A1 | 12/2015 | Pudil |

FOREIGN PATENT DOCUMENTS

| | | |
|---|---|---|
| JP | S5070281 A | 6/1975 |
| JP | S51/55193 | 5/1976 |
| JP | S61164562 | 7/1986 |
| JP | 2981573 | 11/1999 |
| JP | 2005511250 | 4/2005 |
| JP | 200744602 | 2/2007 |
| JP | 200744602 A | 2/2007 |
| JP | 2013502987 | 1/2013 |
| WO | WO 2011/017215 | 2/2011 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

PCT/US2015/019901 International Search Report and Written Opinion dated Jun. 5, 2015.
PCT/US2015/032492 International Search Report dated Nov. 19, 2015.
PCT/US2015/032492 Written Opinion dated Nov. 19, 2015.
Wheaton, et al., Dowex Ion Exchange Resins—Fundamentals of Ion Exchange; Jun. 2000, pp. 1-9. http://www.dow.com/scripts/litorder.asp?filepath=liguidseps/pdfs/noreg/177-01837.pdf.
PCT/US2016/030320 Written Opinion dated Jul. 27, 2016.
Office Action in App. No. AU 2015280604 dated Apr. 8, 2016.
Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
Office Action in App. No. JP 2016-515476 dated Dec. 26, 2016.
Japanese Patent Publication No. S50-70281A.
Japanese Patent Publication No. 2007-44602A.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/019901 Written Opinion dated May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US20115/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 Written Opinion dated Jul. 27, 2016.
PCT/US2016/030319 International Search Report dated Jul. 27, 2016.
PCT/US2016/030320 International Search Report dated Jul. 28, 2016.
PCT/US2016/030320 Written Opinion dated Jul. 28, 2016.
PCT/US2015/032485 Written Opinion dated May 9, 2016.
PCT/US2015/032485 Written Opinion dated Oct. 16, 2015.
PCT/US2016/030320 International Preliminary Report on Patentability, dated Apr. 20, 2017.
PCT/US2015/032494 International Preliminary Report on Patentablity dated Dec. 27, 2016.
[NPL720] PCT/US2015/019901 International Search Report and Written Opinion dated Jun. 5, 2015.
[NPL721] PCT/US2015/019901 International Preliminary Report on Patentability dated May 27, 2016.
PCT/US2016/030304_IPRP.

(56) References Cited

OTHER PUBLICATIONS

[NPL722] PCT/US2015/032494 International Preliminary Report on Patentablity dated Dec. 27, 2016.
[NPL756] European Search Report and Supplemental Search Report in European Application No. 14865374.4 dated June 12, 2017.
European Search Report for App. No. 15812081.6, dated Mar. 8, 2018.
[NPL622] PCT/US2015/032485 Written Opinion dated Oct. 16, 2015.
[NPL696] PCT/US2015/032485 Written Opinion dated May 9, 2016.
European Search Report for EP App. No. 15811326.6, dated Feb. 12, 2018.
European Search Report for EP App. No. 15812413.1, dated Feb. 2, 2018.
PCT/US2016/030319_IPRP.
Search Report in EP App. No. 15752771, dated Nov. 22, 2017.
Office Action in Japanese Application No. 2016-553344, dated Apr. 24, 2018.

RECHARGER FOR RECHARGING ZIRCONIUM PHOSPHATE AND ZIRCONIUM OXIDE MODULES

FIELD OF THE INVENTION

The invention relates to rechargers for recharging sorbent materials within sorbent modules. The rechargers can recharge zirconium phosphate, zirconium oxide, or both zirconium phosphate and zirconium oxide and can be used independently or linked together to share resources and/or infrastructure

BACKGROUND

Zirconium phosphate and zirconium oxide are used in sorbent dialysis to remove waste and unwanted solutes from spent dialysate. Generally, zirconium phosphate removes ammonium, potassium, calcium, and magnesium ions from dialysate while the zirconium oxide removes anions such as phosphate or fluoride ions. Both materials are usually packaged together in a cartridge of some type or packed in separate cartridges. Usually, sorbent cartridges are discarded and replaced after use. The discarded sorbent cartridges are broken down and the individual materials separated from each other. Because zirconium phosphate and zirconium oxide are expensive and rechargeable, sorbent re-processers treat the recovered zirconium phosphate and zirconium oxide with chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Safe disposal of the chemical waste from solutions used to recharge the materials may also require additional steps such as neutralizing the recharging solutions. Conventional methods drive up costs and infrastructure requirements, and increase complexity and waste.

Hence, there is a need for systems and methods that can quickly and effectively recharge sorbent materials without the need to remove the spent sorbent materials from the sorbent cartridge or sorbent modules. There is further a need for systems and methods that can selectively recharge both zirconium phosphate and zirconium oxide either concurrently or independently. There is further a need for systems and methods that can quickly and effectively recharge different sorbent materials within a single recharging system. There is also a need for a system that can recharge both zirconium oxide and zirconium phosphate to allow for automatic neutralization of the recharging solutions allowing safe disposal without additional treatment. The need extends to dual cartridge systems where only one of cartridge is being recharged. There is a need for multiply connectable systems and related methods that can selectively recharge both zirconium phosphate and zirconium oxide for easy and quick use that can scale to use shared resources and/or infrastructure.

SUMMARY OF THE INVENTION

The invention is drawn to a recharger for recharging zirconium oxide and/or zirconium phosphate. In a first aspect, the recharger can have a first receiving compartment for a first sorbent module; the first receiving compartment comprising a first sorbent module inlet and a first sorbent module outlet; one or more fluid sources fluidly connected to the first sorbent module inlet through a first set of one or more fluid connectors; one or more pumps positioned on the one or more fluid connectors for pumping fluid from the one or more fluid sources to the first sorbent module inlet; and a first effluent line fluidly connected to the first sorbent module outlet. In any embodiment, the recharger can have a second receiving compartment for a second sorbent module; the second receiving compartment having a second sorbent module inlet and a second sorbent module outlet; wherein the one or more fluid sources are fluidly connected to the second module inlet through a second set of one or more fluid connectors; one or more pumps positioned on the one or more fluid connectors for pumping fluid from the one or more fluid sources to the second sorbent module inlet; and a second effluent line fluidly connected to the second sorbent module outlet.

In any embodiment, the sorbent module can be a zirconium phosphate module. In any embodiment, the one or more fluid sources can be any one of a water source, a disinfectant source, a brine source, and combinations thereof. The brine source can contain any one of a solution of sodium chloride, sodium acetate, acetic acid, and combinations thereof. In any embodiment, the concentration of sodium chloride can be between 2.5 M and 4.9 M, the concentration of sodium acetate between 0.3 M and 1.1 M, and the concentration of acetic acid between 0.2 M and 0.8 M.

In any embodiment, the sorbent module can be a zirconium oxide module.

In any embodiment, the fluid sources can include a water source, a disinfectant source, and a base source. In any embodiment, the base source can contain sodium hydroxide in a concentration of between 0.5 and 2.0 M. In any embodiment, first effluent line and the second effluent line can be fluidly connected to a drain line. In any embodiment, the drain line can be fluidly connected to any one of a drain, a common reservoir, or combinations thereof In any embodiment, the first sorbent module can be a zirconium phosphate module; and the second sorbent module can be a zirconium oxide module. Alternatively, the first sorbent module can be a zirconium oxide module; and the second sorbent module can be a zirconium phosphate module. In any embodiment, either the first sorbent module or the second sorbent modules can be a zirconium phosphate module; or either the first sorbent module or the second sorbent modules can be a zirconium oxide module.

In any embodiment, the first and second sorbent modules can each be zirconium phosphate module or can each be zirconium oxide modules.

In any embodiment, the recharger can have multiple fluid sources.

In any embodiment, the recharger can have at least one module bypass line; wherein the module bypass line is positioned upstream of the first sorbent module inlet and is fluidly connected to the first effluent line.

In any embodiment, the recharger can have a second module bypass line; wherein the second module bypass line is positioned upstream of the second sorbent module inlet and is fluidly connected to the effluent line.

In any embodiment the drain line can have a static mixer.

In any embodiment, the first module inlet can be fluidly connectable to the first module outlet and/or second module inlet is fluidly connectable to the second module outlet.

In any embodiment, the fluid sources can be selected from the group of a water source, a base source, a disinfectant source, a brine source, and combinations thereof.

In any embodiment, at least one fluid source can be fluidly connected to a second set of one or more connectors in a second recharger.

In any embodiment, either or both of the sorbent module inlet and sorbent module outlet can be positioned on a flexible connector.

In a second aspect, the invention contemplates a dialysis system having one or more sorbent rechargers described in any embodiment wherein the one or more sorbent rechargers are fluidly connected to a common set of the one or more fluid sources. Any features of the first aspect may be included in the second aspect, and any feature of the second aspect can be included in the first aspect.

Any of the features disclosed as being part of the invention can be included in the invention, either alone or in combination.

DETAILED DESCRIPTION OF THE INVENTION

Figure 1:
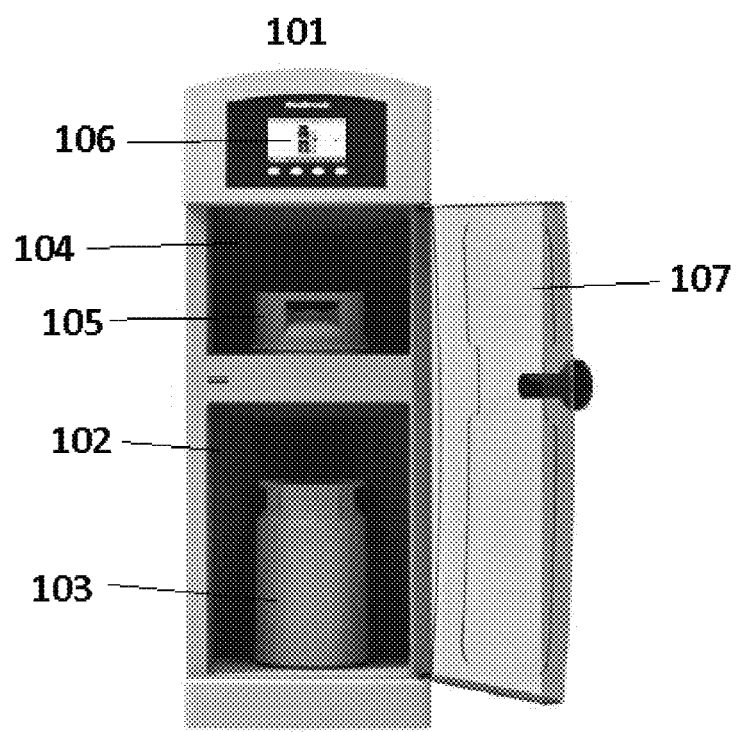
FIG. 1 shows a recharger for recharging zirconium phosphate and zirconium oxide modules.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

A "base source" is a fluid or concentrate source from which a basic solution can be obtained.

A "brine source" is a fluid or concentrate source from which a brine solution can be obtained. As used herein, a brine solution can refer to any solution comprising acids, bases and/or salts.

The term "comprising" includes, but is not limited to, whatever follows the word "comprising." Use of the term indicates the listed elements are required or mandatory but that other elements are optional and may be present.

A "common reservoir" can be a container for collecting from one or more fluid sources including fluid lines or other reservoirs. The "common reservoir" can for example, store used or waste fluids.

The term "common set" refers to sharing any grouping of components, modules, reservoirs, or fluid connectors. For example, a "common set of fluid sources" can refer to shared set of fluid sources that is used by one or more rechargers.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "contain," "containing," or "contained" as used herein means to keep a material within a specific place. "Contain" can refer to materials placed within a component, absorbed onto a component, bound to a component, or any other method of keeping the material in a specific place.

A "disinfectant source" is a fluid or concentrate source from which a disinfectant solution can be obtained. The disinfectant solution can be an acidic solution, such as a peracetic acid solution, or any other solution capable of disinfecting reusable sorbent modules.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain" is a fluid line through which fluids may be disposed.

A "drain line" is a fluid line through which used or waste fluid may flow for disposal. The drain line can be connected to a drain, or to a container or reservoir for later disposal of the fluid.

An "effluent line" is a fluid passageway, tube, or path of any kind into which fluid exiting a container, module, or component will flow.

A "flexible connector" is a connector that can be bent, twisted or otherwise deformed without substantial damage or fluid blockage.

A "fluid" is a liquid substance optionally having a combination of gas and liquid phases in the fluid. Notably, a liquid, as used herein, can therefore also have a mixture of gas and liquid phases of matter.

The term "fluidly connectable," "fluidly connect," "for fluid connection," and the like, refer to the ability of providing for the passage of fluid, gas, or a combination thereof, from one point to another point. The two points can be within or between any one or more of compartments, modules, systems, components, and rechargers, all of any type. The connection can optionally be disconnected and then reconnected.

A "fluid connector," "fluid connection," and the like describe a connection between two components wherein fluid, gas, or a combination thereof, can flow from one component, through a connector or a component for connection, to another component. The connector provides for a fluid connection in its broadest sense and can include any type of tubing, fluid or gas passageway, or conduit between any one or more components of the invention. The connection can optionally be disconnected and then reconnected.

The term "fluid line mixing" refers to mixing fluids at a location or junction wherein flow at the location of junction can, in part, mix one or more fluids.

A "fluid source" is a source from which a fluid or concentrate may be obtained.

The term "mixing" generally refers to causing one or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

A "module bypass line" refers to a fluid line that provides for movement of fluid between two points without passing through a module.

A "module inlet" is a connector through which a fluid, slurry, or aqueous solution can enter a sorbent module.

A "module outlet" is a connector through which a fluid, slurry, or aqueous solution can exit a sorbent module.

The term "positioned" or "position" refers to a physical location of a component or structure.

The term "pump" refers to any device that causes the movement of fluids, gases, or combinations thereof, by applying suction or pressure.

The terms "pumping," "pumped," or to "pump" refers to moving a fluid, gas, or combination thereof, with a pump.

A "receiving compartment" is a space within a recharger into which a sorbent module to be recharged is placed.

A "sorbent recharger" is an apparatus designed to recharge at least one sorbent material.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a sorbent material such as urease. Notably, urease is not "recharged," but can be replenished, as defined herein.

A "recharging flow path" is a path through which fluid can travel while recharging sorbent material in a reusable sorbent module.

The term "solution" refers to a fluid having a solute dissolved in water.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A "static mixer" is a component configured to receive fluids from one or multiple sources and to mix the fluids together. The static mixer may include components that agitate the fluids to further mixing.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "valve" is a device capable of directing the flow of fluid, gas, or a combination thereof, by opening, closing or obstructing one or more pathways to control whether the fluid, gas, or combination thereof, is to travel in a path. One or more valves that accomplish a desired flow can be configured into a "valve assembly."

A "waste reservoir" is a container for collecting and storing used or waste fluids.

A "water source" is a fluid source from which water can be obtained.

A "zirconium oxide module" is a sorbent module containing zirconium oxide.

A "zirconium phosphate module" is a sorbent module containing zirconium phosphate.

Zirconium Phosphate and Zirconium Oxide Rechargers

The invention relates to rechargers that can be used in recharging reusable sorbent modules such as reusable sorbent modules containing zirconium phosphate and/or zirconium oxide. The rechargers described can be used to recharge zirconium phosphate and zirconium oxide in reusable sorbent modules, either concurrently or independently. A recharger can be configured as shown in FIG. 1. The recharger 101 includes a receiving compartment 102 for receiving a reusable zirconium phosphate module 103. Fluid connections (not shown in FIG. 1) connect to the top and bottom of the zirconium phosphate module 103 for passing recharging fluids into, through, and out of the reusable sorbent module 103. As described, the recharging fluids replace ions bound to the sorbent materials during dialysis with new ions, recharging the zirconium phosphate within the zirconium phosphate module 103, allowing reuse of the zirconium phosphate module 103 in dialysis. The recharger 101 also has a second receiving compartment 104 for receiving a reusable zirconium oxide module 105, which is also fluidly connected to recharging fluid sources for recharging of the zirconium oxide module 105. The recharger 101 can be configured to concurrently recharge a zirconium phosphate module 103 and a zirconium oxide module 105, or to independently recharge either a zirconium phosphate module 103 or a zirconium oxide module 105. A user interface 106 is provided to start or control the recharging process by the user. The user interface 106 can also provide the status of the recharging process to the user, such as the time to completion for each recharging step, or a time to complete the entire recharging process. User interface 106 provides alert messages if any problems are detected during recharging, such as leaks, occlusions, pump failures, or mismatched chemicals. A door 107 on the recharger 101 controls access to the receiving compartments 102 and 104 during operation.

In FIG. 1, the receiving compartments 102 and 104 may be of different sizes. Because less zirconium oxide is needed for dialysis than zirconium phosphate, the zirconium oxide module 105 is smaller than the zirconium phosphate module 103 and the receiving compartments 102 and 104 are sized accordingly. The zirconium phosphate receiving compartment 102 can be larger than the zirconium phosphate module 103 and the zirconium oxide receiving compartment 104 can be larger than the zirconium oxide module 105. The larger space allows a user room to maneuver the fluid connectors and sorbent modules to connect the inlets and outlets on the sorbent modules to the inlets and outlets on the recharger 101. Although shown as a recharger for recharging both zirconium phosphate and zirconium oxide in FIG. 1, one of skill in the art will understand that a recharger for recharging solely zirconium oxide or solely zirconium phosphate can be similarly constructed. A recharger for recharging a single sorbent material can have a single receiving compartment or multiple receiving compartments for receiving and recharging multiple modules containing the same sorbent material. Rechargers with any number of receiving compartments for recharging any number or combination of zirconium oxide and/or zirconium phosphate sorbent modules can be constructed. For example, a recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules.

Figure 2:
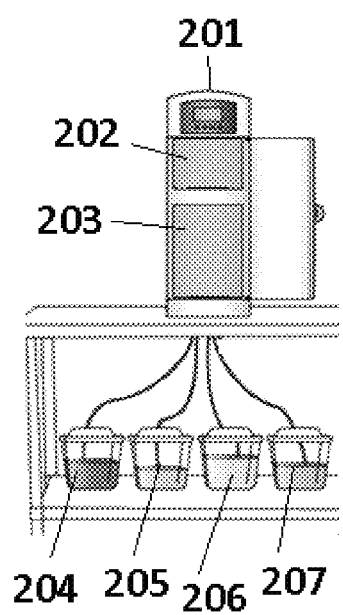
FIG. 2 shows a recharger fluidly connected to external fluid sources.

FIG. 2 illustrates a non-limiting embodiment of a recharger set up for recharging zirconium oxide and zirconium phosphate, either concurrently or independently. To recharge the sorbent materials, one or more recharging fluids can be passed through the reusable sorbent modules. As shown in FIG. 2, the recharger 201 can be fluidly connected to one or more recharging fluid sources, such as water source 204, brine source 205, disinfectant source 206, and base source 207. The recharger has a zirconium phosphate receiving compartment 202 and a zirconium oxide receiving compartment 203. The recharger also has one or more pumps and valves (not shown in FIG. 2) for selectively delivering the recharging fluids from the fluid sources to the reusable modules. As shown in FIG. 2, the recharging fluid sources are housed external to the recharger 201. Alternatively the recharging fluid sources can be housed within the recharger 201. A drain line (not shown) is also connected to the recharger 201 for disposal of waste fluids exiting the reusable modules. The drain line is fluidly connected to a drain, or alternatively, the drain line can be fluidly connected to one or more waste reservoirs for storage and later disposal.

Figure 3:
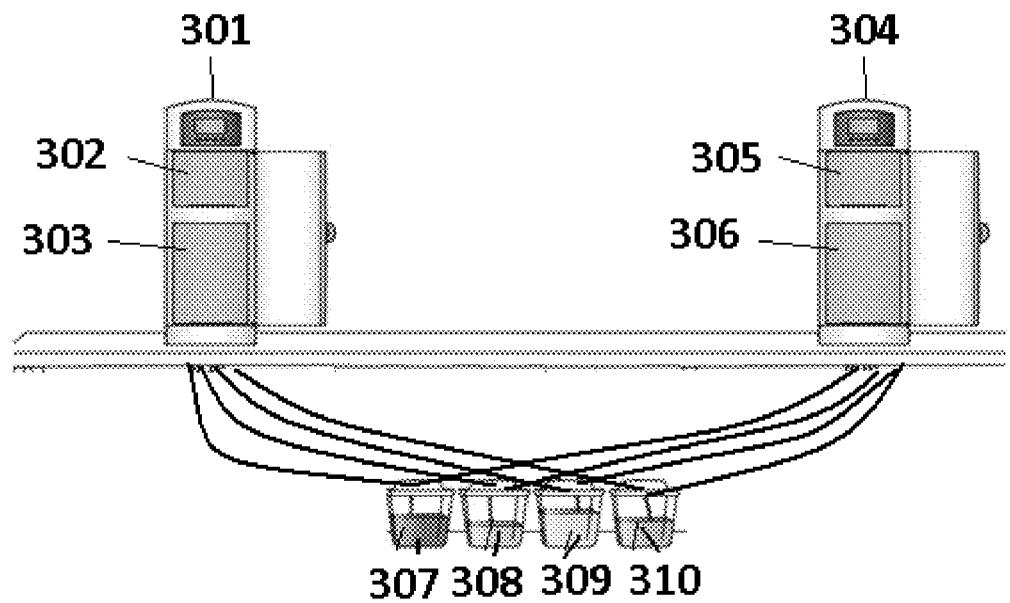
FIG. 3 shows multiple rechargers fluidly connected to a single set of fluid sources.

As illustrated in FIG. 3, multiple rechargers can be chained together and connected to a common set of fluid sources for sharing of infrastructure. A first recharger 301 having a zirconium phosphate receiving compartment 303 and zirconium oxide receiving compartment 302 is fluidly connected to water source 307, brine source 308, disinfectant source 309, and base source 310. A second recharger 304 having a zirconium oxide receiving compartment 305 and zirconium phosphate receiving compartment 306 is also fluidly connected to the same water source 307, brine source 308, disinfectant source 309, and base source 310. Any number of rechargers can be connected to the common set of fluid sources, including 2, 3, 4, 5, 6 or more rechargers, each fluidly connected to a single set of fluid sources and a single set of waste reservoirs. Connecting multiple rechargers to a single set of fluid sources can save space and materials and simplifies recharging multiple sets of reusable modules in a clinic or hospital setting. Each of the rechargers may include a separate drain line and/or separate waste reservoirs, or each recharger may be fluidly connected to a common drain line. The drain line can also be fluidly connected to any one of a drain, a common reservoir, or combinations thereof. Each of the connected rechargers can have separate heaters for heating the brine and/or disinfectant solutions, or centralized heaters can be included, with centralized heating of the shared solutions.

Figure 4:
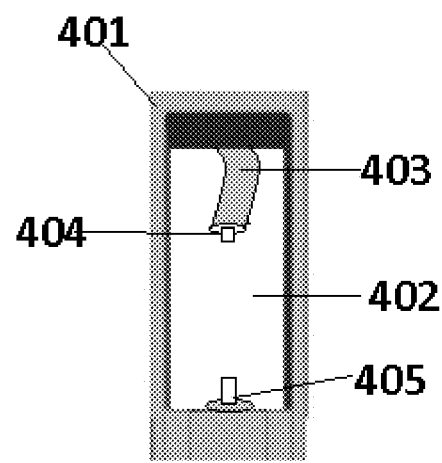
FIG. 4 shows a receiving compartment in a recharger.

FIG. 4 illustrates a non-limiting embodiment of a sorbent module having a single receiving compartment 402 within a recharger 401. The receiving compartment 402 includes a sorbent module inlet 404 on a fluid connector 403. The fluid connector 403 is fluidly connected to the fluid sources, as described, allowing fluid from the fluid sources to enter into the reusable sorbent module. The receiving compartment also includes a sorbent module outlet 405 fluidly connected to an effluent line (not shown in FIG. 4). The effluent line can connect to a drain line, as described. Either or both of the sorbent module inlet 404 and sorbent module outlet 405 can be positioned on a flexible connector, such as fluid connector 403. The flexible connectors allow for easier connection to a reusable sorbent module. Alternative embodiments of a recharger having multiple receiving compartments and flexible connectors are envisioned. The fluid connectors can be sized be of a sufficient length to allow direct connection of the sorbent module inlet 404 to the sorbent module outlet 405. The direct connection between the sorbent module inlet 404 and sorbent module outlet 405 allows for recharging fluids to be passed through the fluid lines of the system even if a sorbent module is not being recharged. As described, when a single module, such as a zirconium oxide module, is being recharged, pumping the zirconium phosphate recharging fluids through the recharger and into a combined drain line allows for in-line neutralization of the zirconium oxide effluent. Alternatively, the same function can be accomplished by including a sorbent module bypass line in the recharging flow paths.

The rechargers can be used in any setting, including a clinic, at home, or in a mobile setting. In any setting, the rechargers can use a water tank or any other source of potable or deionized water. For use in a mobile setting, vans or trucks can carry the rechargers, the disinfectant source, the brine solution, the base solution, and optionally the water, to a location for recharging. For at home use, the brine solution, disinfectant solution, base solution, and optionally the water, may be prepackaged and shipped to a patient. The patient can connect each of the sources to the recharger to allow recharging and reuse of the sorbent modules in dialysis. As described, the rechargers can provide for inline mixing of chemicals, reducing the amount of chemicals required to be moved for use in a mobile setting. Inline mixing of chemicals allows for a smaller amount of concentrated solutions to be moved to a location in a mobile or at home setting, and water from a local water source, such as municipal drinking water, can be used to dilute the disinfectant, base, and/or brine inline. Alternatively, a deionized or purified water source can be provided in a mobile setting. Effluent from the sorbent modules can be collected and neutralized inline for immediate disposal in any drain, or can be collected for later neutralization and disposal offline. The ability to neutralize and dispose of the combined effluents in a drain allow for easier use in an at home or mobile setting, without the need for large waste reservoirs and further treatment.

Figure 5A:
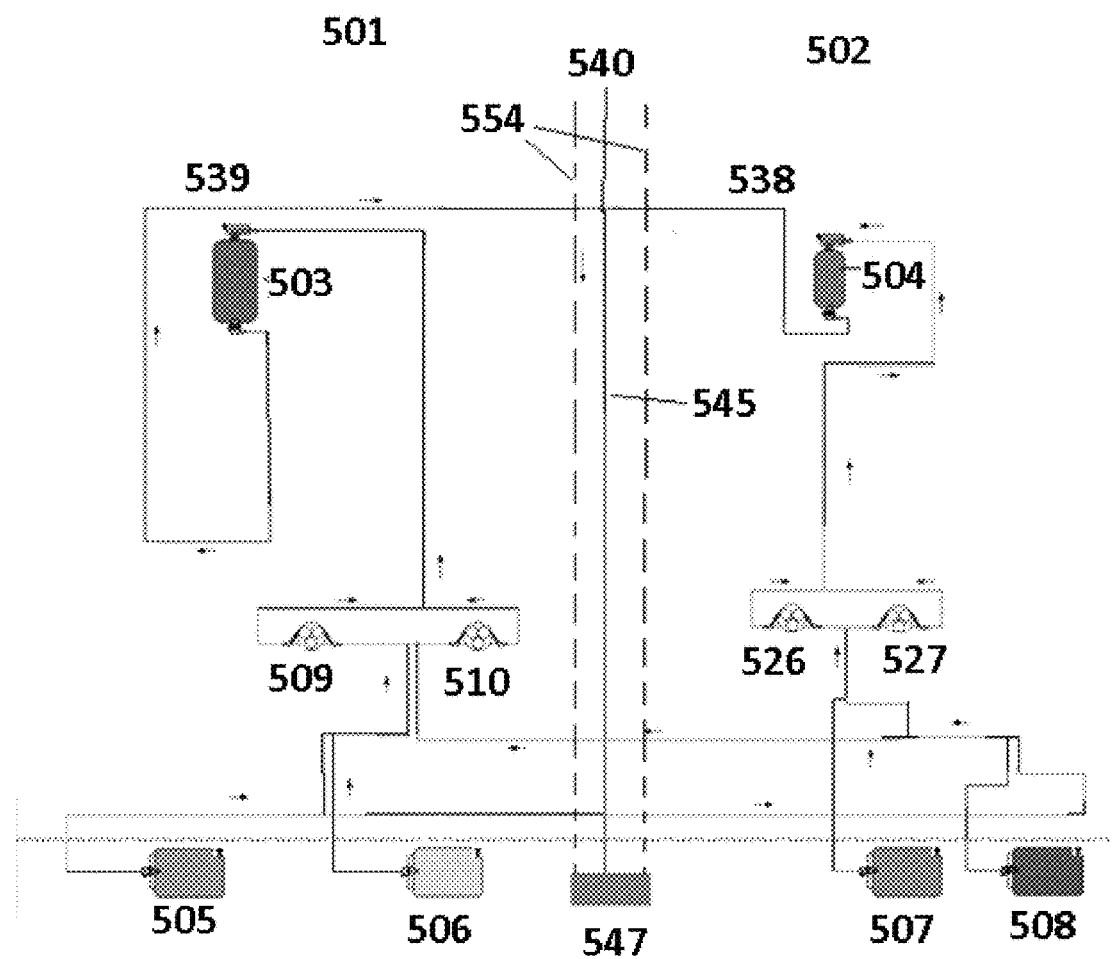
FIG. 5A shows a recharging flow path for recharging zirconium phosphate and zirconium oxide.
Figure 5B:
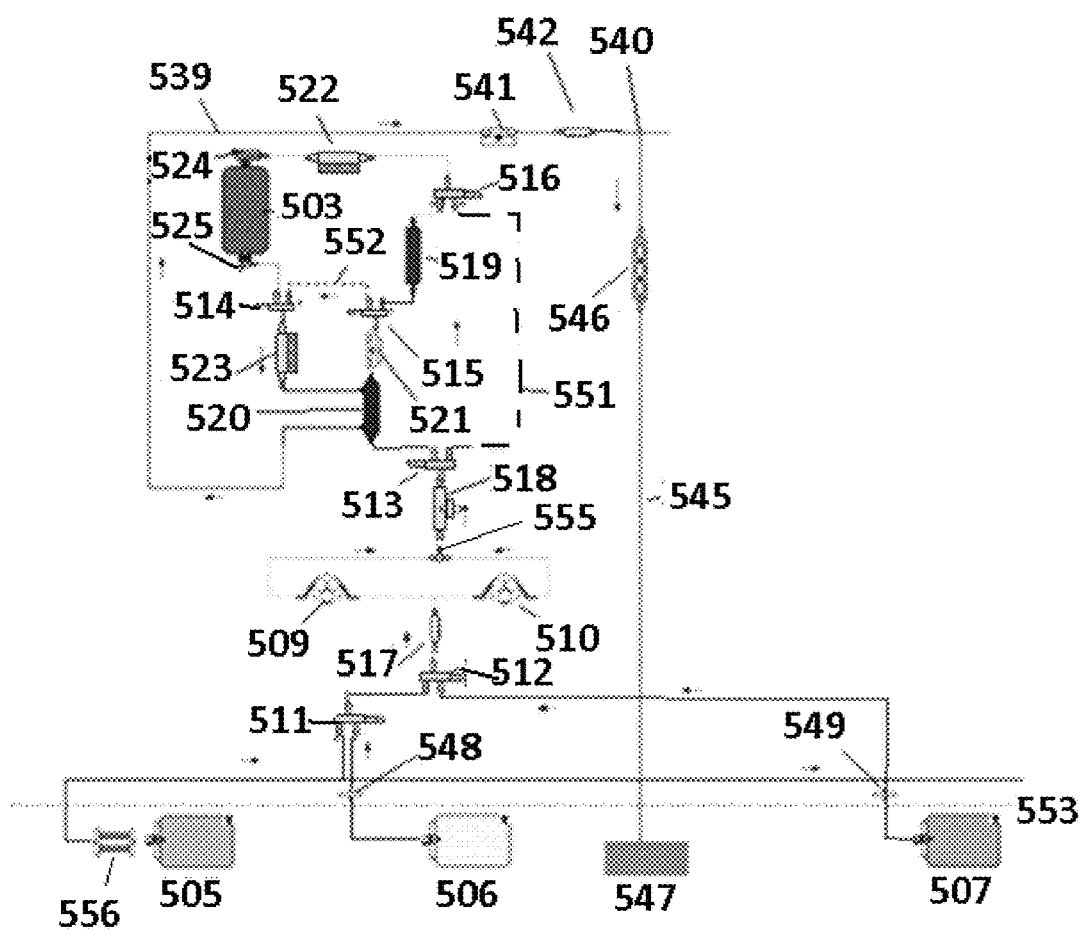
FIG. 5B shows a recharging flow path for recharging zirconium phosphate and is an exploded left side of FIG. 5A.
Figure 5C:
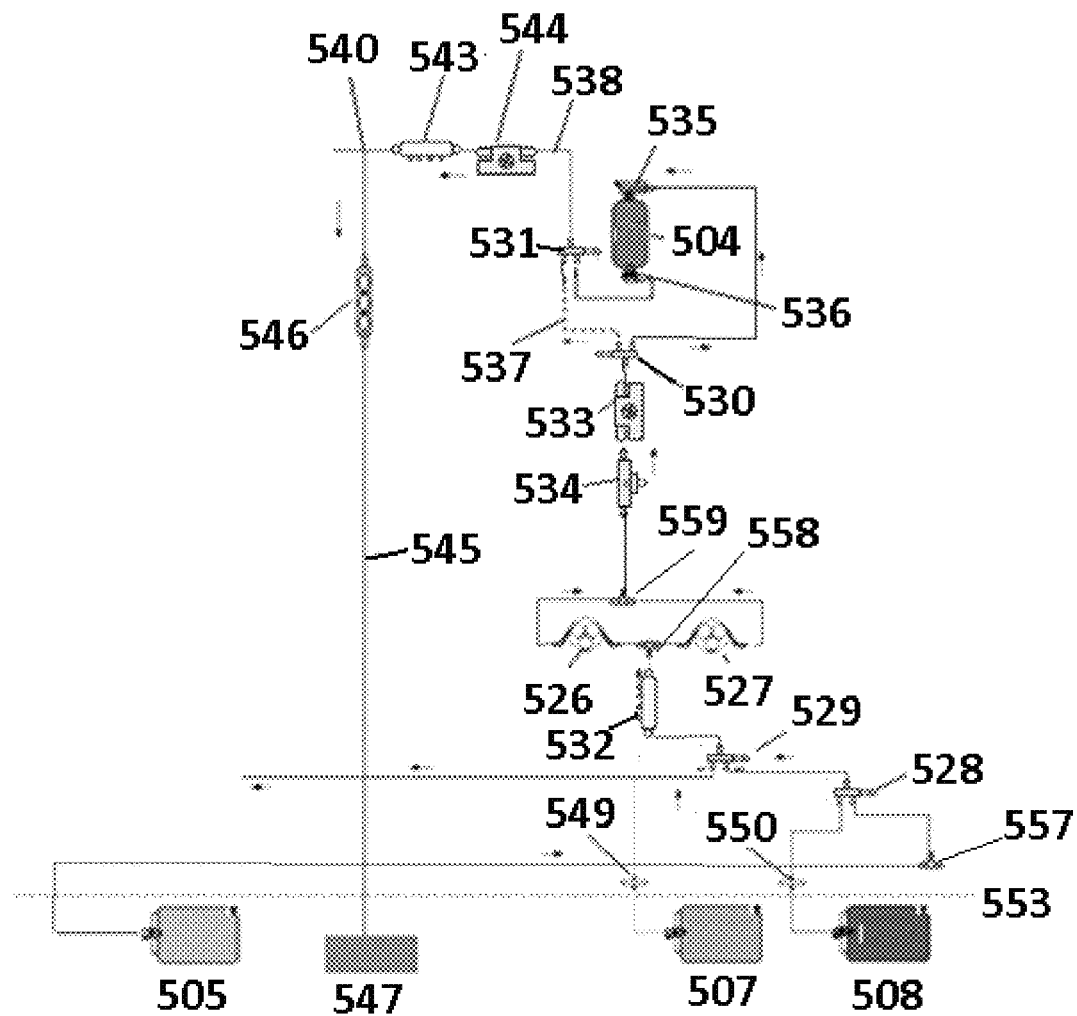
FIG. 5C shows a recharging flow path for recharging zirconium oxide and is an exploded right side of FIG. 5A.

To recharge the sorbent materials, fluids from fluid sources are passed through the sorbent modules. The flow paths of the invention can be arranged as shown in FIGS. 5A-C. FIG. 5A is a generalized view of a recharging flow path, with details shown in FIGS. 5B and 5C. The recharging flow path can be divided into a zirconium phosphate recharging flow path 501 containing the zirconium phosphate module 503 and a zirconium oxide recharging flow path 502 containing zirconium oxide module 504. Details of the zirconium phosphate recharging flow path 501 on the zirconium phosphate side of line 554 are illustrated in FIG. 5B, while details of the zirconium oxide recharging flow path 502 on the zirconium oxide side of line 554 are illustrated in FIG. 5C. Although a dual cartridge recharger system is shown, single, two or more multiple cartridge recharger systems are envisioned. Any one of the recharger cartridge systems can be linked together to share resources for recharging the sorbent cartridge and can be adapted for large scale use. Similarly, the linked rechargers can be scaled down as demand for recharging decreases. The modular recharging set-up having more or less rechargers based on demand can be advantageously used where required.

In FIG. 5A, a zirconium phosphate recharging flow path 501 and a zirconium oxide recharging flow path 502 have a water source 505, a brine source 506, a disinfectant source 507, and a base source 508. The brine source 506, disinfectant source 507, and/or base source 508 can be a column containing a dry bed of the brine, acid, and/or base components. Alternatively, a powdered source of the brine, acid, and/or base components can be used. The dry bed or powdered source can be dissolved with an aqueous solution. A static mixer (not shown) can mix the single line coming through the column prior to entering the zirconium phosphate module 503 or zirconium oxide module 504. Recharging the zirconium phosphate in a zirconium phosphate module 503 requires water, brine, and disinfectant. The water source 505, the brine source 506, and the disinfectant source 507 can be fluidly connected to the zirconium phosphate recharging flow path 501. Similarly, recharging zirconium oxide module 504 in zirconium oxide recharging flow path 502 requires water, base, and disinfectant. The water source 505, the disinfectant source 507, and the base source 508 can be fluidly connected to the zirconium oxide recharging flow path 502. The zirconium phosphate recharging flow path 501 and zirconium oxide recharging flow path 502 can be operated simultaneously or independently. Disinfectant source 507 can contain any type of disinfectant compatible with zirconium phosphate and zirconium oxide capable of disinfecting the reusable sorbent modules. In any embodiment, the acid source 507 can contain peracetic acid. In any embodiment, the peracetic acid can be a solution of between 0.5% and 2% peracetic acid in water. The disinfectant source can alternatively contain any other disinfectant compatible with zirconium phosphate and zirconium oxide modules, including bleach or citric acid. The brine source 506 can have an acid, a base, and a sodium salt.

During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate can be determined by the pH, buffer capacity, and sodium concentration of the brine solution used in the recharging process. The brine source 506 can be a mixture of sodium chloride, sodium acetate, and acetic acid. In one non-limiting brine solution, the sodium chloride concentration can be between 2.5 M and 4.9 M, the sodium acetate concentration can be between 0.3 M and 1.1 M, and acetic acid concentration can be between 0.2 M and 0.8 M. The water source 505 can contain any type of water, including deionized water. To recharge the zirconium phosphate in the zirconium phosphate module 503, the disinfectant from disinfectant source 507 can flow to the zirconium phosphate module 503 to disinfect the zirconium phosphate module 503. Fluid from the disinfectant source 507 can flow to valve 512 in the zirconium phosphate recharging flow path 501. Zirconium phosphate pumps 509 and 510 provide a driving force to pump the fluid through the zirconium phosphate recharging flow path 501. Use of two or more separate pumps can reduce wear on the pumps. Correspondingly, smaller pumps can be used. The two or more pumps can provide in-line mixing and intermittent pumping so at any given time, a single pump can pump fluid through the zirconium phosphate recharging flow path 501. The two pumps can be used simultaneously or independently. The two or more pumps can provide fluid line mixing of one or more separate fluid streams when used simultaneously. The two or more pumps can operate asynchronously but used concurrently. For example, a first pump can operate for a time and a second pump remain off, then the first pump shut off with the second pump turning on. Multiple pumps at various timed pumping stages are envisioned as described herein. One of skill in the art will understand that a single zirconium phosphate pump can also accomplish the described pump functions.

In FIG. 5B, zirconium phosphate pumps 509 and 510 can pump fluid from disinfectant source 507 through valve 512 and valve 513. Fluid can be pumped through three-way junction 555 to valve 516 and into zirconium phosphate module 503 through zirconium phosphate module inlet 524. The illustrated junctions combine the inlet chemicals or water pumped by the two pumps such that higher flow rates can be achieved. During filling, fluid inside zirconium phosphate module 503 can be forced through zirconium phosphate module outlet 525 and into zirconium phosphate module effluent line 539. The disinfectant can be sequestered in the zirconium phosphate module 503 to ensure disinfection. Heater 519 upstream of the zirconium phosphate module 503 can heat the disinfectant because disinfection can become more efficient at elevated temperatures. After disinfection, zirconium phosphate module 503 can be rinsed using water from water source 505. Zirconium phosphate pumps 509 and 510 can pump water from water source 505 through valves 511 and 512 to valve 513. The water can then be pumped through valves 515 and 516 through the zirconium phosphate module 503 through zirconium phosphate module inlet 524, out zirconium phosphate module outlet 525 and into zirconium phosphate module effluent line 539. Water can be pumped through the zirconium phosphate module 503 until all of the disinfectant is removed.

Fluid from brine source 506 can be pumped through the zirconium phosphate module 503 to load the zirconium phosphate module 503 with the proper ratio of sodium and hydrogen ions. Zirconium phosphate pumps 509 and 510 can pump fluid from brine source 506 to valve 511. The brine can follow the same pathway as the water through zirconium phosphate module 503 and into zirconium phosphate module effluent line 539. Heater 519 upstream of the zirconium phosphate module 503 can heat brine because recharging can become more efficient at elevated temperatures. Heat exchanger 520 can lessen the load on heater 519. One or more heat exchangers and one or more heaters can be used. The heat exchanger 520 can be fluidly connected to zirconium phosphate module effluent line 539 and to zirconium phosphate module inlet 524 upstream of heater 519. The heated fluid exiting the zirconium phosphate module 503 in zirconium phosphate module effluent line 539 can heat the incoming brine solution in heat exchanger 520. The heat exchanger 520 can have at least a first chamber and a second chamber. Fluid in the zirconium phosphate inlet lines can pass through the first chamber of the heat exchanger 520, and fluid in the zirconium phosphate effluent line 539 can pass through the second chamber of the heat exchanger 520. The increased temperature of the zirconium phosphate effluent in the second chamber can heat the fluid in the zirconium phosphate inlet lines in the first chamber. The zirconium phosphate module 503 can be rinsed again by pumping water through the zirconium phosphate module 503. A static mixer (not shown) can be positioned upstream of the zirconium phosphate module 503 and mix the solutions prior to entering the zirconium phosphate module 503.

Various sensors can be used in the zirconium phosphate module recharging flow path 501 to ensure proper concentrations and temperatures as shown in FIG. 5B. For example, conductivity sensor 517 can ensure that the incoming water contains no defined level of ions that may interfere with the recharging process, and that the brine solution and disinfectant solution are at a desired concentration. Conductivity sensor 517 can also ensure that sufficient rinsing has occurred to remove brine and disinfectant solution. Pressure sensor 518 can monitor pressure in the zirconium phosphate inlet lines to ensure there are no occlusions or leaks and that the inlet pressures are in an acceptable range. Temperature sensor 522 can ensure that the brine solution is at the proper temperature before entering zirconium phosphate module 503 and to control heater 519. Temperature sensor 523 can be placed in zirconium phosphate module effluent line 539 to monitor the temperature of the effluent which can be controlled by heat exchanger 520 and heater 519. A flow sensor 521 can monitor the flow rates of the fluids in the zirconium phosphate recharging flow path 501 and control zirconium phosphate pumps 509 and 510. One of skill in the art will understand that alternative arrangements of sensors can be used in FIG. 5B and that one or more additional sensors can be added. Further, the sensors can be placed at any appropriate position in the zirconium phosphate recharging flow path 501 to determine fluid parameters at various locations throughout the zirconium phosphate recharging flow path 501.

Zirconium phosphate module bypass line 552 in FIG. 5B fluidly connects valve 515 to valve 514 in the zirconium phosphate effluent line 539. Valves 515 and 516 can be controlled to direct fluid through the zirconium phosphate module bypass line 552 and into zirconium phosphate effluent line 539. The dual flow path aspect of the recharging flow path depicted in FIG. 5A can neutralize the effluent from both the zirconium phosphate module 503 and zirconium oxide module 504 by mixing the acidic effluent from the zirconium phosphate module 503 with the basic effluent from zirconium oxide module 504. If only zirconium oxide module 504 is being recharged using the flow path of FIG. 5C, the zirconium phosphate module bypass line 552 in FIG. 5B can be utilized to direct fluid from the brine source 506 to the zirconium phosphate effluent line 539 to neutralize the zirconium oxide effluent without the need to simultaneously recharge a zirconium phosphate module 503. Alternatively, zirconium phosphate module inlet 524 can directly connect to zirconium phosphate module outlet 525. The zirconium phosphate recharging flow path 501 can include a rinse loop 551 to fluidly connect valve 513 upstream of the heater 519 and heat exchanger 520 to valve 516, bypassing heater 519 and heat exchanger 520. The rinse loop 551 can rinse brine solution from the zirconium phosphate module 503. By bypassing heater 519 and heat exchanger 520 through rinse loop 551, the zirconium phosphate module 503 can be cooled faster.

In FIG. 5C, the zirconium oxide module 504 can be recharged by pumping disinfectant from disinfectant source 507 to the zirconium oxide module 504 to disinfect the zirconium oxide module 504. Fluid from the disinfectant source 507 can be pumped to valve 529 in the zirconium oxide recharging flow path 502. Zirconium oxide pumps 526 and 527 can pump fluid through the zirconium oxide recharging flow path 502. As described, a single zirconium oxide pump is contemplated as an alternative to the dual pump system in FIG. 5C. Also, more than two zirconium oxide pumps are contemplated. The two or more zirconium oxide pumps can provide fluid line mixing of one or more separate fluid streams when used simultaneously. The two or more pumps can be asynchronous but used concurrently. For example, a first pump can operate for a time and a second pump remain off, then the first pump shut off with the second pump turning on. Multiple pumps at various timed pumping stages are envisioned as described herein. Zirconium oxide pumps 526 and 527 of FIG. 5C pump fluid from disinfectant source 507 through valve 529 to valve 530. The fluid can flow to the zirconium oxide module 504 through zirconium oxide module inlet 535. During filling, fluid inside zirconium oxide module 504 can flow through zirconium oxide module outlet 536 and into zirconium oxide module effluent line 538. The disinfectant can be sequestered in zirconium oxide module 504 to ensure disinfection. The zirconium oxide module 504 can then be flushed with water from water source 505 after disinfection is completed. Zirconium oxide pumps 526 and 527 can pump water from water source 505 through valves 528 and 529 and junction 557 to valve 530. The fluid passes through junctions 558 and 559 to reach valve 530. The water can then be pumped to zirconium oxide module 504 through zirconium oxide module inlet 535 and out zirconium oxide module outlet 536 and into zirconium oxide module effluent line 538. The zirconium oxide module 504 can be flushed with any volume of water required to ensure that the disinfectant is completely removed.

In FIG. 5C, zirconium oxide pumps 526 and 527 can pump fluid from base source 508 through valve 528 to zirconium oxide module 504. The base source 508 can contain hydroxide ions to recharge zirconium oxide module 504. The hydroxide ions can flow through zirconium oxide module 504 and into zirconium oxide module effluent line 538. The base source 508 can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.5 M and 2.0 M. Another non-limiting example is sodium hydroxide having a concentration at 90% or greater than 2% of the concentration of the recharging solution. A final rinse of the zirconium oxide module 504 can be performed by pumping water through the zirconium oxide recharging flow path 502 of FIG. 5A and zirconium oxide module 504. Zirconium oxide recharging flow path 502 can also have a zirconium oxide module bypass line 537 fluidly connecting valve 530 in the zirconium oxide inlet line to valve 531 in the zirconium oxide effluent line 538 as shown in FIG. 5C Valves 530 and 531 can direct fluid through the zirconium oxide module bypass line 537 and into zirconium oxide effluent line 538. Zirconium oxide module bypass line 537 can convey fluid directly from the base source 508 to the zirconium oxide effluent line 538 to neutralize the zirconium phosphate effluent without the need to simultaneously recharge a zirconium oxide module 504. Alternatively, zirconium oxide module inlet 535 can be fluidly connected to zirconium oxide module outlet 536. Multiple sensors can be included in the zirconium oxide recharging flow path 502 to monitor fluid concentration. For example, conductivity sensor 532 can monitor concentrations of the zirconium oxide recharging fluid; pressure sensor 534 can monitor pressure in the zirconium oxide inlet line and to detect leaks or occlusions. Flow sensor 533 can determine the flow rate of the fluid through the zirconium oxide inlet line and be used to control zirconium oxide pumps 526 and 527. A static mixer (not shown) can be positioned upstream of the zirconium oxide module 504 and mix solutions prior to entering the zirconium oxide module 504. A heater and heat exchanger (not shown) can be positioned in the zirconium oxide recharging flow path 502 to heat fluids prior to entering zirconium oxide module 504. Heating fluid in the zirconium oxide recharging flow path 502 can reduce recharging times and allow disinfection with a base solution, such as sodium hydroxide. Heating the fluid also allows for reduced disinfection time with an acid source. A zirconium oxide rinse loop (not shown) can also be included to bypass the heater and heat exchanger during flushing.

Effluent from zirconium phosphate recharging flow path 501 can neutralize, either completely or in part, the effluent from zirconium oxide recharging flow path 502, and vice versa. Zirconium phosphate effluent line 539 can be fluidly connected to zirconium oxide effluent line 538 at an effluent line junction 540 joining drain line 545, which fluidly connects to drain 547. Static mixer 546 can be used at or downstream of the effluent line junction 540 to mix zirconium phosphate effluent with zirconium oxide effluent.

Zirconium phosphate effluent line 539 of FIG. 5B and zirconium oxide effluent line 538 of FIG. 5C can be connected to a common reservoir for storage and disposal of the combined effluent. The common reservoir can receive and collect the zirconium phosphate and zirconium oxide effluents together. The collected effluents can be drained after appropriate volumes of each effluent have been added to achieve neutralization. A common reservoir can allow for neutralization of the zirconium phosphate and zirconium oxide effluents without synchronizing the recharging processes. A single common reservoir can be sized to support multiple recharge stations. Alternatively, the two fluid streams may be mixed through fluid line mixing at the effluent line junction 540. Flow sensor 541 and conductivity sensor 542 can be placed in zirconium phosphate effluent line 539 to measure the flow rate and composition of the zirconium phosphate effluent as shown in FIG. 5B. Similarly, flow sensor 544 and conductivity sensor 543 can be positioned in the zirconium oxide effluent line 538 to measure the flow rate and composition of the zirconium oxide effluent of FIG. 5C. Data from flow sensors 541 and 544 and conductivity sensors 542 and 543 can determine if the combined effluent in drain line 545 is safe for disposal into a drain. One non-limiting example of safe is an effluent having a pH 5-9. Either zirconium phosphate effluent line 539 or zirconium oxide effluent line 538 can be connected simultaneously or independently to a waste reservoir (not shown) for disposal. Additional pH or conductivity sensors can be positioned downstream of the static mixer 546 to monitor and ensure safe disposal. Drain line 545 can also be connected to a common waste reservoir for storage and disposal of effluent. The common reservoir receives and collects the zirconium phosphate and zirconium oxide effluents together. The collected effluents can be drained after appropriate volumes of each effluent have been added to achieve neutralization. A common waste reservoir advantageously allows for neutralization of the zirconium phosphate and zirconium oxide effluents without synchronizing the recharging processes. Static mixer 546 can be unnecessary when a common reservoir is used.

Brine source 506, disinfectant source 507, and base source 508 can have filter 548, filter 549, and filter 550, respectively to remove particulate matter. The one or more filters can remove particulate matter before fluid enters the zirconium oxide recharging flow path 502 or zirconium phosphate recharging flow path 501. Water source 505 can have microbial filter 556 to remove microbes from the water before entering the flow paths. In FIG. 5C, the dashed line 553 represents a recharger housing. The fluid sources can be external to the recharger housing and fluidly connected to the lines located inside of the recharger housing. Alternatively, the fluid sources described can instead be housed within the recharger.

During recharging, fluid can be passed through the zirconium phosphate module 503 and/or the zirconium oxide module 504 opposite to a flow direction used during dialysis. For example, zirconium phosphate module inlet 524 can be used as the zirconium phosphate module outlet during dialysis, and zirconium phosphate module outlet 525 can be used as the zirconium phosphate module inlet during dialysis in FIG. 5B. Similarly, zirconium oxide module inlet 535 in FIG. 5C can be used as the zirconium phosphate module outlet during dialysis, and zirconium oxide module outlet 536 can be used as the zirconium phosphate module inlet during dialysis. Pumping the recharging fluid through the modules in the opposite direction relative to dialysis can improve the efficiency of the recharging process.

The zirconium phosphate recharging flow path 501 or zirconium oxide recharging flow path 502 of FIG. 5A can independently recharge zirconium phosphate or zirconium oxide. For example, a single flow path fluidly connecting zirconium phosphate module 503 of FIG. 5B via valve 512 and valve 513 to each of the water source 505, brine source 506, and disinfectant source 507 can independently recharge the zirconium phosphate module 503. Similarly, a single flow path fluidly connecting zirconium oxide module 504 of FIG. 5C via valve 528 and valve 529 to each of the water source 505, disinfectant source 507, and base source 508 can independently recharge the zirconium oxide module 504.

The water source 505, brine source 506, disinfectant source 507, and base source 508 can recharge one or more reusable sorbent module of various sizes. The amount of water, brine, disinfectant, and base depends on the concentration of each of the recharging solutions, the size of the reusable sorbent modules, the amount of cations/anions removed, and the flow rate used to pass the solutions through the reusable modules. The amount of brine solution required can depend on the temperature to which the brine solution is heated. For example, a brine solution having between 2.5 M and 4.9 M sodium chloride, between 0.3 M and 1.1 M sodium acetate, and between 0.2 M and 0.8 M acetic acid at between 70° C. and 90° C. requires between 4.2-6.2 L of brine to recharge a zirconium phosphate module containing between 2 kg and 3.2 kg of zirconium phosphate loaded with 2 to 3 moles of ammonium, calcium, magnesium and potassium. The brine solution should have a volume of at least between 4.2 and 6.2 L and delivered at a flow rate of between 100 and 300 mL/min. A single brine source can be connected to multiple rechargers, or can recharge multiple zirconium phosphate modules in a single recharger. The brine source can have a significantly larger volume from 1-100× or greater to ensure that the brine source need not be refilled each time a zirconium phosphate is recharged. For a zirconium oxide module having between 220 and 340 g of zirconium oxide loaded with 200 mmols of phosphate, a base source having between 0.5 and 2.0 M sodium hydroxide and a flow rate between 30 and 150 mL/min requires between 1 and 4 L of base. The base source can be at least between 1 and 4 L in volume. For recharging multiple zirconium oxide modules, a larger base source can be used.

Figure 6A:
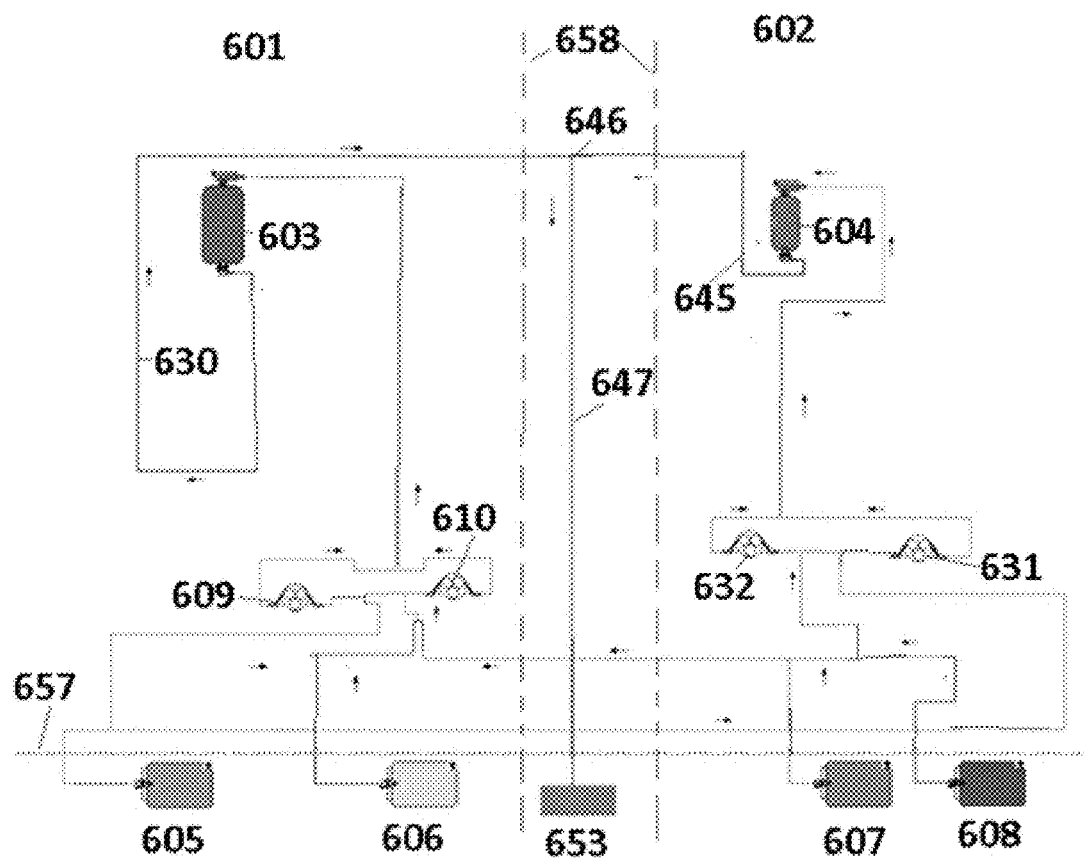
FIG. 6A shows a recharging flow path for recharging zirconium phosphate and zirconium oxide with in-line mixing of recharging solutions.
Figure 6B:
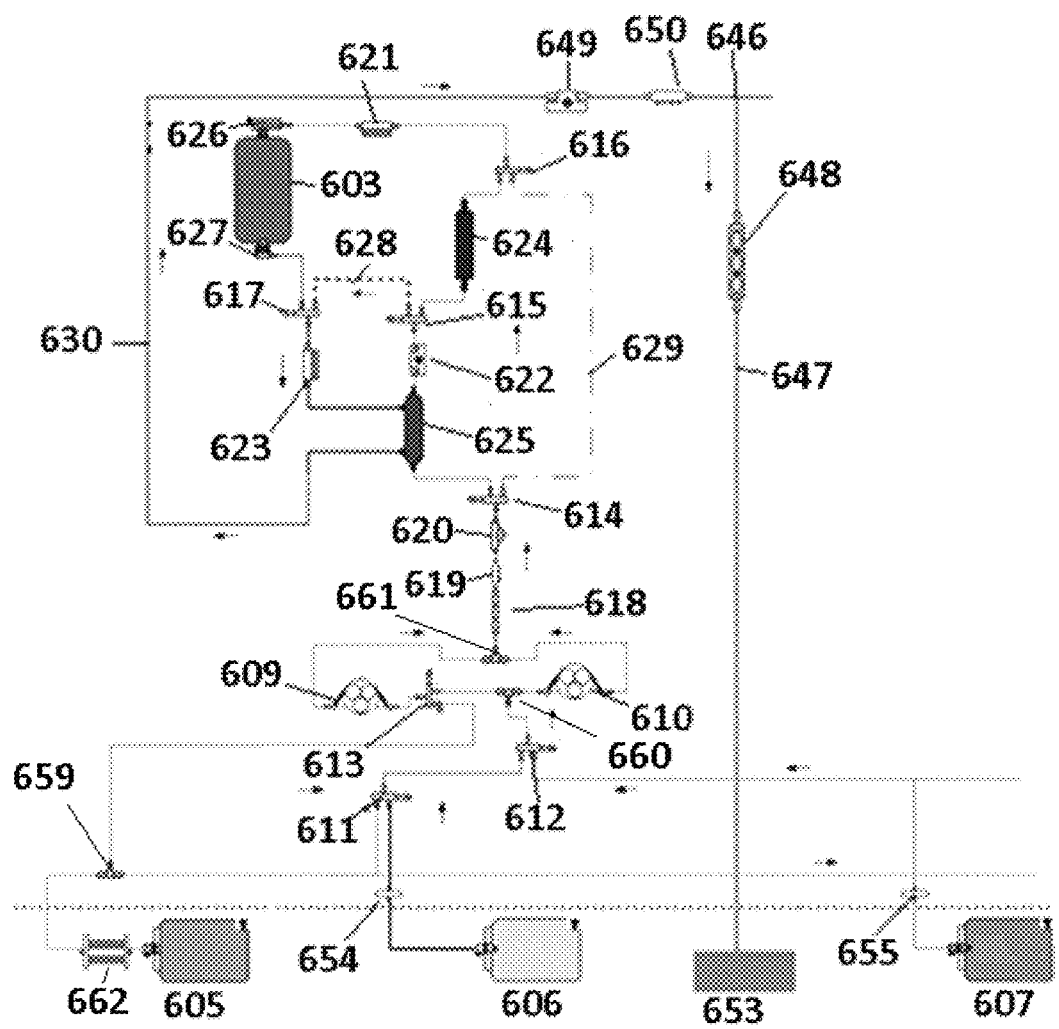
FIG. 6B shows a recharging flow path for recharging zirconium phosphate with in-line mixing of recharging solutions and is an exploded right side of FIG. 6A.
Figure 6C:
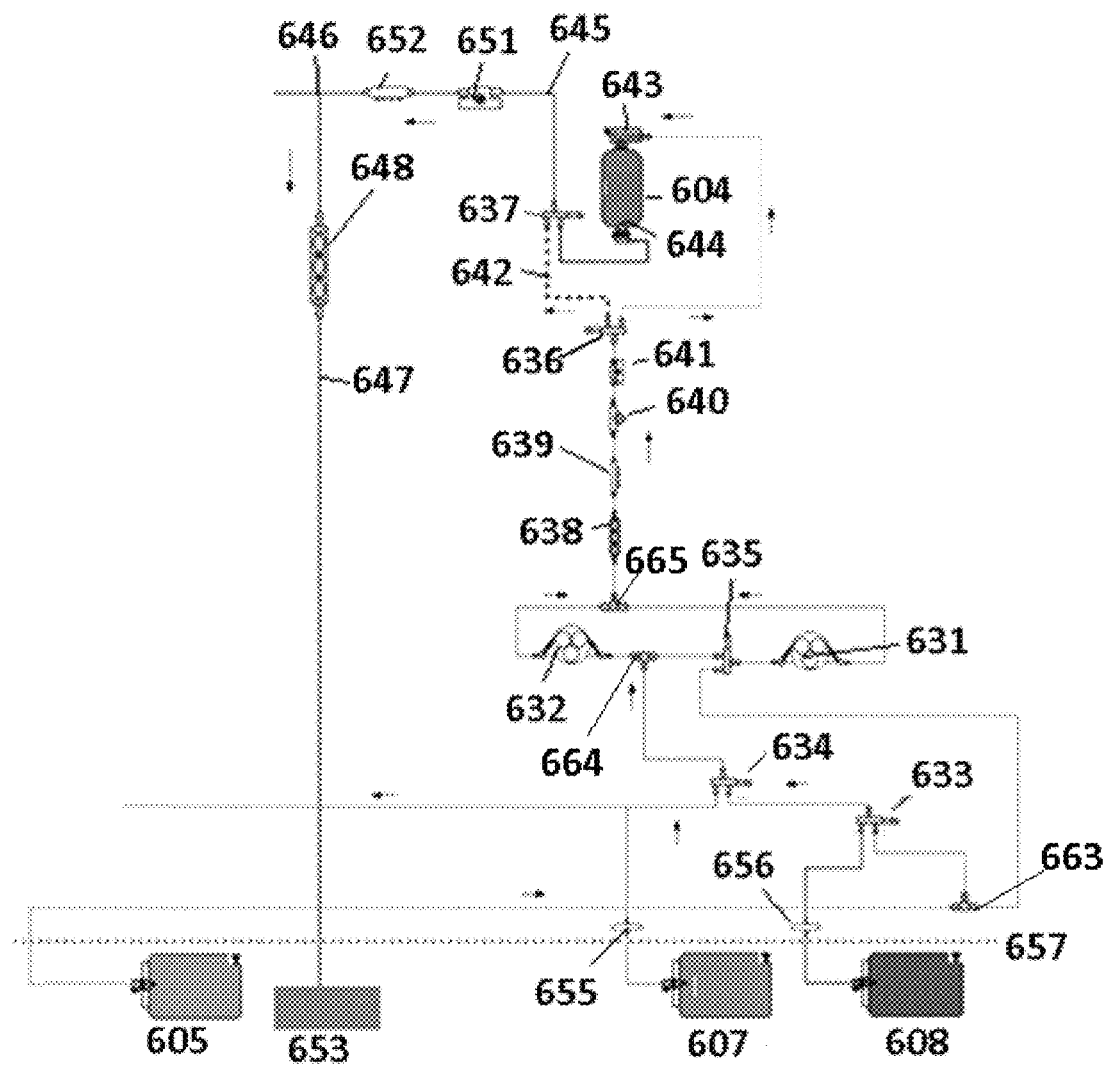
FIG. 6C shows a recharging flow path for recharging zirconium oxide with in-line mixing of recharging solutions and is an exploded left side of FIG. 6A.

FIG. 6A is a generalized view of a recharging flow path having a zirconium phosphate recharging flow path 601 containing a zirconium phosphate module 603 and a zirconium oxide recharging flow path 602 containing a zirconium oxide module 604 with in-line mixing of recharging solutions. FIG. 6B illustrates a detailed view of zirconium phosphate recharging flow path 601 on the zirconium phosphate side of line 658, and FIG. 6C illustrates a detailed view of zirconium oxide recharging flow path 602 on the zirconium oxide side of line 658. The valves, pumps and static mixers illustrated in FIGS. 6B and 6C allow for inline mixing of the recharging fluids. In FIG. 6A, the zirconium phosphate recharging flow path 601 and/or zirconium oxide recharging flow path 602 can be simultaneously or independently connected to a water source 605, a brine source 606, a disinfectant source 607, and a base source 608. Because recharging of the zirconium phosphate in a zirconium phosphate module 603 can require water, brine, and disinfectant, and because recharging of zirconium oxide in zirconium oxide module 604 can also require water, base, and disinfectant, the water source, 605, the brine source 606, and the disinfectant source 607 can be jointly connected to the zirconium phosphate recharging flow path 601, and the water source 605, the disinfectant source 607, and the base source 608 can be jointly connected to the zirconium oxide recharging flow path 602.

In FIG. 6A, zirconium phosphate recharging flow path 601 and zirconium oxide recharging flow path 602 can mix chemicals in-line to create the recharging solutions. Any of disinfectant source 607, brine source 606, and base source 608 can contain solutions having concentrations over the concentration of the components to be used in recharging the reusable modules. Water source 605 can dilute the disinfectant, brine, and base from the fluid sources prior to recharging. In FIG. 6B, zirconium phosphate pump 610 can pump disinfectant into the zirconium phosphate module 603 with in-line mixing of concentrated disinfectant from disinfectant source 607 from valve 612 through junctions 660 and 661 and into static mixer 618. Concurrently, zirconium phosphate pump 609 can pump water through junction 659 and valve 613 and into static mixer 618 from water source 605. Alternatively, the concentrated disinfectant and water can be mixed through fluid line mixing at the junction of the two fluid lines as shown in line junction 646 of FIG. 6A. The zirconium phosphate pumps 609 and 610 can pump a disinfectant solution having a specified concentration and composition to disinfect the zirconium phosphate module 603 via valves 612 and 613 of FIG. 6B. The disinfectant solution can flow from static mixer 618 through valve 614 to valve 616 and then into the zirconium phosphate module 603 through zirconium phosphate module inlet 626. Fluid can exit zirconium phosphate module 603 through zirconium phosphate module outlet 627 into zirconium phosphate effluent line 630. After disinfection of zirconium oxide module 603, zirconium phosphate pumps 609 and 610 can pump water from water source 605 into zirconium phosphate module 603. For example, zirconium phosphate pump 609 can pump water through valve 613 to zirconium phosphate module 603 while zirconium phosphate pump 610 can pump water through valves 611 and 612 to zirconium phosphate module 603. Alternatively, zirconium phosphate pump 609 can pump water through valves 611, 612, and 613 while zirconium phosphate pump 610 pumps water through valves 611 and 612. During recharging, zirconium phosphate pumps 609 and 610 can pump brine through valve 611 to valve 612 from brine source 606 into static mixer 618. If a concentrated brine solution is being used, zirconium phosphate pumps 609 and/or 610 can pump water from water source 605 to static mixer 618 to dilute the brine solution and generate a brine solution having a proper solute concentration for recharging the zirconium phosphate. After pumping brine through the zirconium phosphate module 603, zirconium phosphate pump 609 can pump water through valves 611, 612 and 613 while zirconium phosphate pump 610 can pump water through valve 611 and 612.

The zirconium phosphate recharging flow path 601 of FIG. 6B can have a heater 624 and heat exchanger 625. One or more heat exchangers and one or more heaters can be used. The brine solution can be heated by the heater 624 upstream of the zirconium phosphate module 603. Heat exchanger 625 can utilize the heat from brine exiting the zirconium phosphate module 603 to heat the incoming brine solution upstream of heater 624 to reduce the burden on heater 624. As described, the zirconium phosphate recharging flow path 601 can also have an optional zirconium phosphate module bypass line 628 fluidly connecting valve 615 in the zirconium phosphate inlet line to valve 617 in the zirconium phosphate effluent line 630. The zirconium phosphate module bypass line 628 can neutralize the zirconium oxide effluent with brine even if the zirconium phosphate module 603 is not being recharged. Zirconium phosphate recharging flow path 601 can have a rinse loop 629 connecting valve 614 upstream of the heater 624 and heat exchanger 625 to valve 616 to bypass heater 624 and heat exchanger 625 to rinse brine out of the zirconium phosphate module 603.

Various sensors can be included in the zirconium phosphate recharging flow path 601 to ensure fluid parameters are within acceptable ranges. In FIG. 6B, conductivity sensor 619 can be placed downstream of static mixer 618 to ensure mixing and specified recharging fluid concentrations. Pressure sensor 620 can measure the fluid pressure and to identify leaks or occlusions. Flow sensor 622 can determine the flow rate of the fluid entering the zirconium phosphate module 603 and be used to control zirconium phosphate pumps 609 and 610. Temperature sensor 621 can determine if the recharging fluid is a proper temperature range upon entering zirconium phosphate module 603 and relay data to a processor (not shown) that can control heater 624. Temperature sensor 623 can determine the temperature of the zirconium phosphate effluent prior to entering heat exchanger 625. Other sensor arrangements, including any number of conductivity, pressure, flow, and temperature sensors can be used.

In FIG. 6C, zirconium oxide pump 632 can pump disinfectant from disinfectant source 607 through valve 634 and into static mixer 638 to disinfect the zirconium oxide module 604 in zirconium oxide recharging flow path 602. Zirconium oxide pump 631 can pump water from water source 605 through valve 635 to static mixer 638 to dilute the disinfectant from disinfectant source 607 to provide in-line mixing of the disinfectant solution. The diluted disinfectant can then be pumped through valve 636 to zirconium oxide module inlet 643 and into zirconium oxide module 604. Effluent from the zirconium oxide module 604 can exit through zirconium oxide module outlet 644 and into zirconium oxide effluent line 645. After disinfection, the disinfectant can be rinsed from the zirconium oxide module 604 by pumping water from water source 605 through valve 635 to zirconium oxide module 604 by zirconium oxide pump 631 while zirconium oxide pump 632 pumps water through valves 633 and 634 to zirconium oxide module 604. Alternatively, zirconium oxide pump 631 can pump water through valves 633, 634, and 631, while zirconium oxide pump 632 pumps water through valves 633 and 634. To recharge zirconium oxide module 604, zirconium oxide pump 632 can pump base from base source 608 through valves 633 and 634 through junctions 664 and 665 to static mixer 638. Water from water source 605 can be pumped by zirconium oxide pump 631 through junctions 663 and 665 into static mixer 638 to dilute the base by in-line mixing. Alternatively, the water and base can be mixed through fluid line mixing at the junction of the two fluid lines. Alternatively, the base can be pre-set using specified amounts of base in pre-packaged packets or containers. Diluted base can flow through the zirconium oxide recharging flow path 602 and through zirconium oxide module 604. The zirconium oxide module 604 can be rinsed any numbers of times, as needed, by introducing water from water source 605 to the zirconium oxide module 604. The zirconium oxide recharging flow path 602 can also have a zirconium oxide module bypass line 642 that fluidly connects valve 636 to valve 637 in the zirconium oxide effluent line 645 to bypass zirconium oxide module 604. In this way, zirconium phosphate effluent can be neutralized with a base solution even if the zirconium oxide module 604 is not being recharged. A heater and heat exchanger (not shown) can be positioned in the zirconium oxide recharging flow path 602 to heat fluids prior to entering zirconium oxide module 604. A zirconium oxide rinse loop (not shown) can also be included to bypass the heater and heat exchanger. Similarly, the zirconium oxide recharging flow path 602 can also have sensors for measurement and control over the recharging process. In FIG. 6C, a conductivity sensor 639 can be placed downstream of static mixer 638 to ensure that diluted recharging solutions have a desired concentration. Pressure sensor 640 can detect the pressure in the zirconium oxide recharging flow path 602 to detect leaks or occlusions. Flow sensor 641 can detect the flow rate of fluid in the zirconium oxide recharging flow path 602 and can be used to control zirconium oxide pumps 631 and 632.

As shown in FIG. 6A, the present invention can provide in-line neutralization of the effluent from each of the zirconium phosphate recharging flow path 601 and zirconium oxide recharging flow path 602. The zirconium phosphate effluent line 630 can be fluidly connected to zirconium oxide effluent line 645 at effluent line junction 646 and fluidly connected to drain line 647. As shown in FIGS. 6B and 6C, a static mixer 648 can be positioned at or downstream of the effluent line junction 646 to ensure mixing of the effluents from the zirconium phosphate recharging flow path 601 and zirconium oxide recharging flow path 602. The combined effluent can be passed through the drain line 647 to drain 653, or to a common waste reservoir (not shown), or to separate waste reservoirs. A conductivity sensor 650 as shown in FIG. 6B in zirconium phosphate effluent line 630 and a conductivity sensor 652 as shown in FIG. 6C in zirconium oxide effluent line 645 can determine the composition of the effluents. Flow sensor 649 in zirconium phosphate effluent line 630 of FIG. 6B and flow sensor 651 in zirconium oxide effluent line 645 of FIG. 6C can be used simultaneously or independently to measure the flow rates of each of the effluents. Determining the composition of the effluent fluids as well as the respective flow rates using one or more sensors described can monitor the system function and ensure that the combined effluent in drain line 647 is safe for disposal or storage.

Brine source 606, disinfectant source 607, and base source 608 can have filter 654, filter 655, and filter 656, respectively to remove particulate matter prior to entering zirconium phosphate recharging flow path 601 or zirconium oxide recharging flow path 602. The filters can also act as inline mixers to mix the solutions. Water source 605 can have microbial filter 662 to remove microbes from the water. Brine source 606, disinfectant source 607, and base source 608 can be housed outside of a recharger housing denoted by line 657. The brine solution, disinfectant solution, and base solution can be generated through in-line mixing as described. Alternatively, pre-mixed solutions, concentrates, or infusates can be introduced into brine source 606, disinfectant source 607, and base source 608 and delivered to zirconium phosphate recharging flow path 601 or zirconium oxide recharging flow path 602. For example, the brine solution in brine source 606 can be pre-mixed or provide in pre-packaged amounts in the proper concentrations and introduced into brine source 606, disinfectant source 607, and base source 608.

In-line mixing can provide higher concentrations of solutes, lower fluid volumes required by the system, and physically smaller fluid reservoirs. The fluids can have suitable concentrations for use in the zirconium phosphate recharging flow path 601 or zirconium oxide recharging flow path 602. For example, an initially high source of peracetic acid can be used in a concentration of between 20% and 40%. The zirconium phosphate recharging flow path 601 of FIG. 6B can dilute the peracetic acid or other disinfectant source by a factor of 20:1 to 40:1 to generate an disinfectant solution having a concentration between 0.5% and 2%. The initial disinfectant concentration can be any concentration greater than 1%. Similarly, the base solution can be sodium hydroxide having an initial concentration between 14 M and 22 M. The zirconium oxide recharging flow path 602 of FIG. 6C can dilute the base solution by 18:1 to 22:1 to generate a base solution having a concentration between 0.8 and 1.0 M. The initial base solution concentration can be any concentration greater than or equal to 0.5 M. The brine solution can also be diluted in-line to generate a brine solution having a proper recharging concentration. The brine source 606 of FIG. 6A can be one or more reservoirs. For example, an acetic acid source, a sodium acetate source and a sodium chloride source can each be connected in place of single brine source 606. Alternatively, an acetic acid source, a base source, and a sodium chloride source can be connected in place of the single brine source 606 with mixing of the base and acetic acid to generate the sodium acetate. The individual components can be added to the zirconium phosphate recharging flow path 601 in the proper ratios to generate the recharging brine.

The chemicals used in the recharging process can be packaged and shipped in any form. The chemicals can be packaged and shipped as solutions, either in proper concentrations for use in recharging or with higher concentrations for use in in-line mixing. In any embodiment, the chemicals may be packaged and shipped in pure form, such as 100% acetic acid or solid sodium chloride, sodium acetate, or sodium hydroxide.

Figure 7:
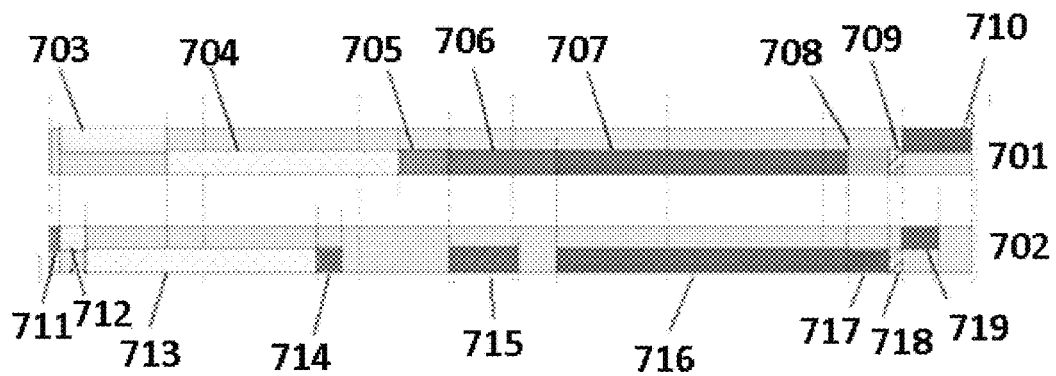
FIG. 7 shows a timeline for concurrent recharging of zirconium oxide and zirconium phosphate.

FIG. 7 illustrates a non-limiting example of a timeline that can be used for concurrent or separate recharging of zirconium phosphate and zirconium oxide. Timeline 701 shows recharging zirconium phosphate and timeline 702 shows recharging zirconium oxide. As illustrated in timeline 701, the zirconium phosphate recharging process can begin by introducing a disinfectant, such as peracetic acid, into the zirconium phosphate module, shown as step 703. The time necessary to fill the zirconium phosphate module with the disinfectant can depend on the flow rate of the disinfectant solution and the volume of the zirconium phosphate module. The disinfectant can be delivered to the zirconium phosphate module in step 703 at a flow rate of between 200 and 500 mL/min, which can fill a zirconium phosphate module in a time of between 5-10 minutes. After filling the zirconium phosphate with the disinfectant solution, the disinfectant solution can be held in the zirconium phosphate module to ensure disinfecting of the zirconium phosphate module in step 704. In any embodiment, the disinfectant can be held in the zirconium phosphate module for any length of time sufficient to disinfect the zirconium phosphate module, including between 5 and 20 minutes. Longer or shorter flushing times can be used depending on the need. The temperature of the disinfectant can be determined with a temperature sensor, and the hold time adjusted as necessary. For example, if the disinfectant temperature is 22° C., the hold time can be 5 minutes. The disinfectant can also be heated to minimize the hold time by heating the disinfectant to room temperature. During the hold time, the disinfectant flow can be stopped or reduced to a low flow condition, such as 5 to 75 ml/min. Holding the disinfectant, such as peracetic acid, in the module can build up pressure in the module, requiring periodic venting. To maintain the volume after venting, during which some fluid may leak, the disinfectant can be pumped into the module at a low flow rate during the venting. Alternatively, during the hold time, the disinfectant flow rate can be set to between 5 and 75 ml/min to prevent pressure buildup while maintaining fluid volume in the modules. The disinfectant solution can then be flushed from the zirconium phosphate module in step 705 by pumping water through the zirconium phosphate module. The water can flow through the zirconium phosphate module at a specified rate. A higher flow rate of the water in step 705 will cause a quicker flush time. The water can be pumped through the zirconium phosphate module at a rate of between 100 and 500 mL/min. Depending on the size of the zirconium phosphate module, the zirconium phosphate module can be flushed in about 5-10 minutes. As described, the system can utilize one or more sensors, such as pH sensors or conductivity sensors in the zirconium phosphate effluent lines to determine if disinfectant is fully flushed in step 705. After flushing the disinfectant from the zirconium phosphate module in step 705, brine solution can be pumped through the zirconium phosphate module to recharge the zirconium phosphate module starting in step 706. The brine solution can be pumped through the zirconium phosphate module in step 706 at any rate. One of skill in the art will understand that a higher flow rate of brine solution may decrease the time necessary to recharge the zirconium phosphate, but may also decrease the efficiency of the process, resulting in the need for additional brine. Conductivity or pH sensors can determine if the zirconium phosphate module has been fully filled with brine.

The brine flow rate can be set to any flow rate, including between 150 and 250 mL/min. Depending on the size of the zirconium phosphate module, between 5 and 10 minutes may be needed for brine to reach the sensors in the zirconium phosphate effluent line. Once brine has reached the sensors in the effluent line, the brine can flow through the zirconium phosphate module in step 707 until recharging is complete. Recharging time can vary based on the flow rate of the brine solution, the concentration of the brine solution, and the temperature of the brine solution. For example, the brine solution can be heated during the recharging process between 65° C. and 95° C. Recharging of zirconium phosphate can be more efficient at elevated temperatures. Conductivity sensors can be used to determine if step 708 has been completed by detecting the conducting of the fluid in the zirconium phosphate effluent line. If the conductivity of the effluent matches the conductivity of the brine, then no additional ions from the brine are being exchanged onto the zirconium phosphate, and recharging is complete. For example, steps 708, 709, and 710 represent brine solution being flushed from the zirconium phosphate module with water. Flushing can continue through step 710 until the conductivity sensors in the zirconium phosphate effluent line determine no additional brine is being removed from the zirconium phosphate module.

As depicted in timeline 702, zirconium oxide can be recharged concurrently or independently of zirconium phosphate. In step 711, zirconium oxide recharging begins by rinsing the zirconium oxide module with water. The water rinse can flush leftover dialysate bicarbonate or any sodium hydroxide from the flow loop, which may react violently with acid necessary for disinfection. After flushing the zirconium oxide module with water in step 711, disinfectant solution can be delivered to disinfect the module in step 712. The time necessary to fill the zirconium oxide module with disinfectant depends on the size of the zirconium oxide module and the flow rate of the disinfectant. Because less zirconium oxide is needed for dialysis than zirconium phosphate, the zirconium oxide module may be smaller than the zirconium phosphate module, and therefore fill faster in step 712 as compared to the zirconium phosphate module in step 703. Upon filling, the disinfectant can be sequestered in the zirconium oxide module to allow for disinfection in step 713. The disinfectant can be held in the zirconium oxide module for any length of time, including between 5 and 20 minutes. The temperature of the disinfectant can be determined with a temperature sensor, and a hold time adjusted as necessary. For example, if the disinfectant temperature is 22° C., the hold time can be 5 minutes. The disinfectant can also be heated to minimize the necessary hold time. Upon disinfection, the disinfectant can be flushed from the zirconium oxide module in step 714.

In step 715 the base solution flows through the zirconium oxide module to recharge the zirconium oxide. Step 715 continues until a basic solution is detected in the zirconium oxide effluent line. During simultaneous recharging, the basic effluent from the zirconium oxide recharging flow path neutralizes the acidic effluent from the zirconium phosphate recharging flow path. Once a basic effluent is detected in step 715, the zirconium oxide recharging process can be halted until the acid brine is detected in the effluent of the zirconium phosphate module in step 706, which may occur later due to size differences of the zirconium phosphate and zirconium oxide modules. After the acidic effluent is detected in the zirconium phosphate module, shown as step 706, the base can continue to flow through the zirconium oxide module in step 716. The flow rate of the base solution in step 716 can be any suitable rate. For example, the flow rate of the base solution can be between 30 and 150 mL/min. To ensure neutralization, the flow rate of the base in step 716 can depend on the flow rate of the brine in step 707. As described, the base and effluent are each brought to a point equidistant to a junction between the zirconium phosphate and zirconium oxide effluent lines. Based on the conductivity of each effluent, the pumping is restarted at a ratio of speed that is needed for neutralization. The ratio could be 1:1 or any other ratio. Although described as using a conductivity sensor, the system can alternatively use a pH sensor or a combination of pH and conductivity sensors. A neutralization ratio can be calculated based on the relative pH, buffer capacity, and concentration of the zirconium phosphate effluent and zirconium oxide effluent. For example, a neutralization ratio of 1.5:1 means that 1.5 liters of the zirconium phosphate effluent will be required to fully neutralize one liter of zirconium oxide effluent. The flow rate of the base in step 716 can be set to half the flow rate of the brine solution, allowing full neutralization of both solutions. For example, the flow rate of the base in step 716 can be between 75 and 125 mL/min if the neutralization ratio is 1.5:1 and the brine flow rate is between 150 and 250 mL/min.

After the brine solution is detected in the effluent of the zirconium phosphate and the flushing of the brine begins in step 708, the base solution can pass through the zirconium oxide module, shown as step 717 until the brine is mostly or fully flushed from the zirconium phosphate module, shown as step 709. At this point, the base solution can be flushed from the zirconium oxide module, shown as step 718. After confirming that the base has been flushed from the zirconium oxide module, flushing is completed in step 719.

One of skill in the art will understand that the times and flow rates described in FIG. 7 can be altered within the scope of the invention. Higher flow rates can cause faster recharging of the modules. Times can be decreased by using more concentrated solutions, but may decrease efficiency. Specified concentrations, flow rates, and times can be set per the needs of the user, taking into account the cost of chemicals and need for fast recharging. The times and flow rates shown in zirconium oxide recharging timeline 702 can also be altered to reduce idle time. For example, the flow rate of the base solution in step 715 can be slowed down to reduce the time gap between steps 715 and 716. If a single sorbent module is being recharged independently, or if a common reservoir is used for the zirconium phosphate and zirconium oxide recharging flow paths either inside or outside of the recharger, the times and flow rates shown in FIG. 7 can be adjusted. Synchronizing the zirconium phosphate timeline 701 with the zirconium oxide timeline 702 is unnecessary because effluent is no longer neutralized in-line.

Figure 8:
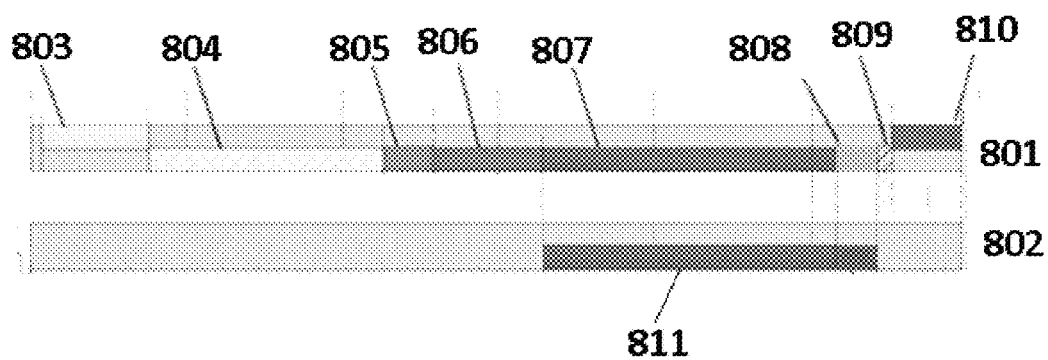
FIG. 8 shows a timeline for independent recharging of zirconium phosphate.

FIG. 8 illustrates a non-limiting example of a timeline that can be used for independent recharging of zirconium phosphate using the dual recharging flow path described herein. Timeline 801 shows recharging zirconium phosphate and timeline 802 shows the process for in-line neutralization without recharging a zirconium oxide module. As illustrated in timeline 801, the zirconium phosphate recharging process can begin by introducing a disinfectant, such as peracetic acid, into the zirconium phosphate module, shown as step 803. After filling the zirconium oxide with the disinfectant solution, the disinfectant solution can be sequestered in the zirconium oxide module to ensure disinfecting of the zirconium phosphate module in step 804. The disinfectant solution can then be flushed from the zirconium phosphate module in step 805 by pumping water through the zirconium phosphate module at a specified rate. As described, the system can utilize one or more sensors, such as pH sensors or conductivity sensors in the zirconium phosphate effluent lines to determine if disinfectant is fully flushed in step 805. After flushing the disinfectant from the zirconium phosphate module in step 805, brine solution can be pumped through the zirconium phosphate module to recharge the zirconium phosphate module starting in step 806. Once brine has reached the sensors in the effluent line, the brine can flow through the zirconium phosphate module in step 807 until recharging is complete. At the same time, a base solution can be pumped through the zirconium oxide recharging flow path in step 811 to neutralize the brine solution.

As described, conductivity sensors can be used to determine if step 808 has been completed by detecting the conducting of the fluid in the zirconium phosphate effluent line. If the conductivity of the effluent matches the conductivity of the brine, then no additional ions from the brine are being exchanged onto the zirconium phosphate, and recharging is complete. For example, steps 808, 809, and 810 represent brine solution being flushed from the zirconium phosphate module with water. Flushing can continue through step 810 until the conductivity sensors in the zirconium phosphate effluent line determine no additional brine is being removed from the zirconium phosphate module. Once the conductivity sensors determine that the pH of the zirconium phosphate effluent is safe for disposal without additional treatment, the base solution in the zirconium oxide recharging flow path is stopped. The fluid flow rates and concentrations used in the process illustrated in FIG. 8 can be the same as the fluid flow rates and concentrations described with reference to FIG. 7.

Figure 9:
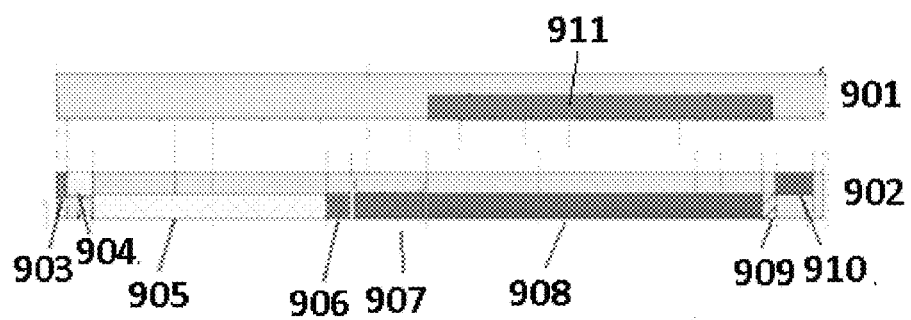
FIG. 9 shows a timeline for independent recharging of zirconium oxide.

FIG. 9 shows a timeline for independently recharging zirconium oxide. Timeline 902 shows the recharging of zirconium oxide and timeline 901 shows using the zirconium phosphate recharging flow path for in-line neutralization of the zirconium oxide effluent. In step 903, zirconium oxide recharging begins by rinsing the zirconium oxide module with water to flush leftover dialysate bicarbonate, which may react violently with acid necessary for disinfection. After flushing the zirconium oxide module with water in step 903, disinfectant solution can be delivered to disinfect the module in step 904. Upon filling, the disinfectant can be sequestered in the zirconium oxide module to allow for disinfection in step 905. Upon disinfection, the disinfectant can be flushed from the zirconium oxide module in step 906.

In step 907 the base solution flows through the zirconium oxide module to recharge the zirconium oxide. Step 907 continues until a basic solution is detected in the zirconium oxide effluent line. Once the basic solution is detected in the zirconium oxide effluent line, brine is pumped through the zirconium phosphate recharging flow path for in-line neutralization of the basic zirconium oxide effluent in step 911. The base solution continues to flow through the zirconium oxide module until recharging is complete in step 908. After recharging the zirconium oxide in step 908, the basic solution can be flushed in steps 909 and 910. Conductivity sensors in the zirconium oxide effluent line determine when the basic solution is fully flushed, at which point the brine solution in step 911 can be stopped. The process illustrated in FIG. 9 can use the same flow rates and concentrations as described with respect to FIG. 7.

The zirconium oxide and zirconium phosphate sorbent modules can be recharged and reused any number of times. Alternatively, the sorbent modules may have a defined useful life, including a maximum number of recharge and reuse cycles. When a sorbent module reaches the end of the sorbent module's useful life, the sorbent module can be recycled or disposed of. A disinfection only cycle can disinfect the sorbent modules for safe disposal and/or recycling at the end of the sorbent module's useful life. In a disinfection only cycle, the disinfectant can be pumped into the sorbent module as described but the other recharge solutions would not be used. After disinfection, and optionally rinsing of the sorbent module, the sorbent module can be disposed or recycled safely.

Figure 10:
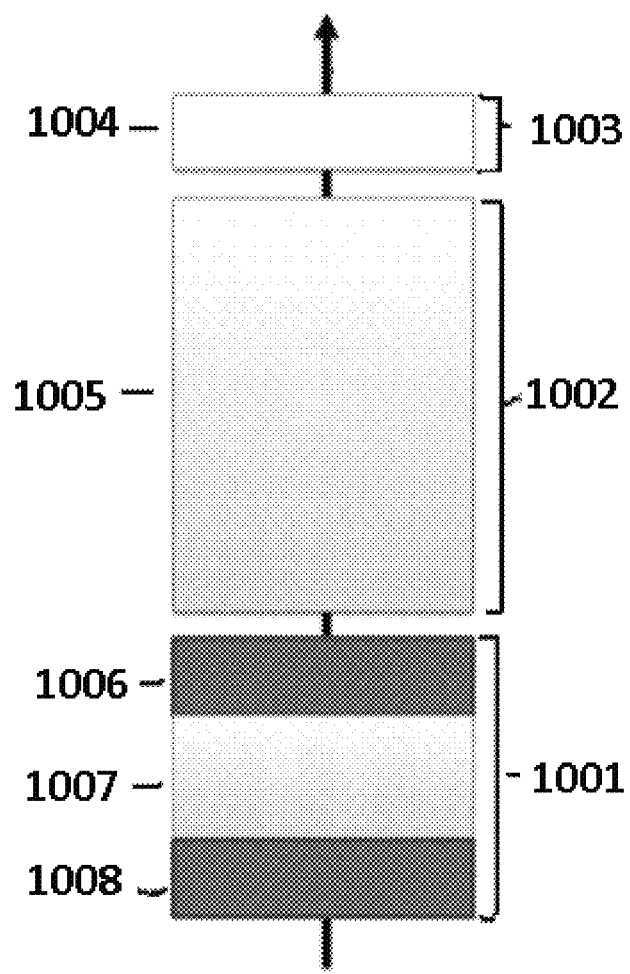
FIG. 10 shows material layers in a module sorbent cartridge including reusable modules.

A non-limiting embodiment of a reusable sorbent cartridge having modules that can be separated and recharged by systems and methods of the present invention is shown in FIG. 10. The sorbent cartridge can be separated into reusable modules to facilitate recharging of one or more sorbent materials. In FIG. 10, the sorbent cartridge has a first sorbent module 1001, a second sorbent module 1002, and a third sorbent module 1003. The first module 1001 can have a layer of activated carbon 1008, a layer of alumina and urease 1007, and a second layer of activated carbon 1006. The activated carbon can remove many non-ionic solutes from the dialysate. The urease catalyzes the conversion of urea in the dialysate into ammonium ions. The alumina can serve as a support for the urease. The second layer of activated carbon 1006 can capture any urease that migrates out of alumina and urease layer 1007 prior to exiting the first module 1001. The first module 1001 can be a single use module, or can be a multiple use module with replenishment of the urease. The second module 1002 can have zirconium phosphate 1005. After dialysis, zirconium phosphate 1005 will contain bound potassium, calcium, magnesium, and ammonium ions, which can be replaced with sodium and hydrogen ions by the recharging process described herein. Third module 1003 can contain zirconium oxide 1004. After use, the zirconium oxide 1004 will contain bound phosphate, fluoride and other anions, which can be replaced with hydroxide anions through the recharging process described herein. The flow direction of flow of dialysate through the sorbent cartridge is shown by the arrow in FIG. 10. The recharging solutions can also flow through the reusable sorbent modules in an opposite direction to improve the efficiency of the recharging process.

Figure 11:
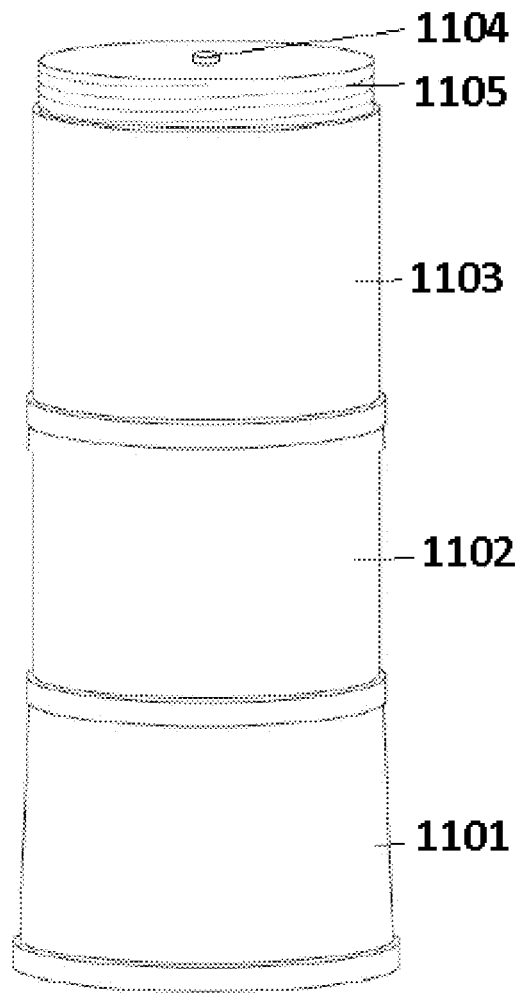
FIG. 11 shows multiple sorbent modules connected together to form a sorbent cartridge.

FIG. 11 illustrates another non-limiting example of a modular sorbent cartridge that can be used in the recharging process described herein. The modular sorbent cartridge can be separated into discrete modules including a first module 1101, a second module 1102, and a third module 1103 connected together to form a sorbent cartridge. The first module 1101 can contain activated carbon, urease, and alumina; the second module 1102 can contain zirconium phosphate; and the third module 1103 can contain zirconium oxide. One of skill in the art will understand that the modular sorbent cartridge illustrated in FIG. 11 is for illustrative purposes only, and modifications to the sorbent cartridge can be made within the scope of the invention. Alternatively, the sorbent modules can be independent with fluid lines connecting each of the sorbent modules for dialysis. During dialysis, dialysate can enter the sorbent cartridge through the bottom of first module 1101, travel through modules 1101, 1102, and 1103, and exit through fluid outlet 1104. The fluid outlet 1104 can connect to the rest of the dialysate flow path. Threaded portion 1105 on module 1103 can be used in connecting modules to each other, to the dialysate flow path, or to the recharger as described herein. The threaded portion 1105 can be included on any of the sorbent modules. Other connection types suitable for secured fluid connection in dialysis known in the art is contemplated by the invention. For example, fluid lines can be clamped directly onto fluid outlet 1104. After dialysis, a user can disconnect the sorbent modules for disposal of single use modules and for recharging of the reusable modules.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A sorbent recharger, comprising:
at least a first receiving compartment for a first sorbent module; the first receiving compartment having a first sorbent module inlet and a first sorbent module outlet;
one or more fluid sources fluidly connected to the first sorbent module inlet through a first set of one or more fluid connectors; the one or more fluid sources containing fluid capable of recharging a sorbent material within the first sorbent module;
one or more pumps positioned on the one or more fluid connectors for pumping fluid from the one or more fluid sources to the first sorbent module inlet; and
a first effluent line fluidly connected to the first sorbent module outlet;
the sorbent recharger configured to recharge the sorbent material within the first sorbent module.

2. The sorbent recharger of claim 1, further comprising:
at least a second receiving compartment for a second sorbent module; the second receiving compartment having a second sorbent module inlet and a second sorbent module outlet;
one or more fluid sources fluidly connected to the second module inlet through a second set of one or more fluid connectors; and
one or more pumps positioned on the one or more fluid connectors for pumping fluid from the one or more fluid sources to the second sorbent module inlet; and
a second effluent line fluidly connected to the second sorbent module outlet.

3. The sorbent recharger of claim 1, wherein the first sorbent module is a zirconium phosphate module.

4. The sorbent recharger of claim 3, wherein the one or more fluid sources is any one of a water source, a disinfectant source, and a brine source.

5. The sorbent recharger of claim 4, wherein the one or more fluid sources comprise a brine source, and wherein the brine source contains any one of a solution of sodium chloride, sodium acetate, acetic acid, and combinations thereof.

6. The sorbent recharger of claim 5, wherein the concentration of sodium chloride is between 2.5 M and 4.9 M, the concentration of sodium acetate is between 0.3 M and 1.1 M, and the concentration of acetic acid is between 0.2 M and 0.8 M.

7. The sorbent recharger of claim 2, wherein the second sorbent module is a zirconium oxide module.

8. The sorbent recharger of claim 7, wherein the one or more fluid sources is any one of a water source, a disinfectant source, a base source, and combinations thereof.

9. The sorbent recharger of claim 8, wherein the one or more fluid sources comprise a base source, and wherein the base source contains sodium hydroxide in a concentration of between 0.5 M and 2.0 M.

10. The sorbent recharger of claim 2, wherein the first effluent line and the second effluent line are fluidly connected to a drain line.

11. The sorbent recharger of claim 10, wherein the drain line is fluidly connected to any one of a drain, a common reservoir, or combinations thereof.

12. The sorbent recharger of claim 2, wherein the first sorbent module is a zirconium phosphate module; and the second sorbent module is a zirconium oxide module.

13. The sorbent recharger of claim 2, wherein the first sorbent module is a zirconium oxide module; and the second sorbent module is a zirconium phosphate module.

14. The sorbent recharger of claim 2, wherein the first and second sorbent modules are each zirconium phosphate modules or each zirconium oxide modules.

15. The sorbent recharger of claim 2, further comprising at least one module bypass line; wherein the module bypass line is positioned upstream of the first sorbent module inlet and is fluidly connected to the first effluent line.

16. The sorbent recharger of claim 15, further comprising at least a second module bypass line; wherein the second module bypass line is positioned upstream of the second sorbent module inlet and is fluidly connected to the second effluent line.

17. The sorbent recharger of claim 11, wherein the drain line has a static mixer.

18. The sorbent recharger of claim 2 wherein either or both of:
    the first module inlet is fluidly connectable to the first module outlet; and
    the second module inlet is fluidly connectable to the second module outlet.

19. The sorbent recharger of claim 10, wherein the fluid sources are selected from the group consisting of a water source, a base source, a disinfectant source, a brine source, and combinations thereof.

20. The sorbent recharger of claim 1, wherein the at least one fluid source is fluidly connected to a second set of one or more connectors in a second recharger.

21. The sorbent recharger of claim 1, wherein either or both of the sorbent module inlet and sorbent module outlet are positioned on a flexible connector.

22. A dialysis system, comprising:
    one or more of the sorbent recharger of claim 1, wherein the one or more sorbent rechargers are fluidly connected to a common set of the one or more fluid sources.

* * * * *